(12) United States Patent
Maeda et al.

(10) Patent No.: US 7,232,639 B2
(45) Date of Patent: Jun. 19, 2007

(54) MONOMER HAVING FLUORINE-CONTAINING ACETAL OR KETAL STRUCTURE, POLYMER THEREOF, AND CHEMICAL-AMPLIFICATION-TYPE RESIST COMPOSITION AS WELL AS PROCESS FOR FORMATION OF PATTERN WITH USE OF THE SAME

(75) Inventors: Katsumi Maeda, Tokyo (JP); Kaichiro Nakano, Tokyo (JP)

(73) Assignee: NEC Corporation (JP)

( * ) Notice: Subject to any disclaimer, the term of this patent is extended or adjusted under 35 U.S.C. 154(b) by 0 days.

(21) Appl. No.: 10/505,799

(22) PCT Filed: Feb. 25, 2003

(86) PCT No.: PCT/JP03/02031

§ 371 (c)(1),
(2), (4) Date: Aug. 25, 2004

(65) Prior Publication Data
US 2005/0164119 A1 Jul. 28, 2005

(51) Int. Cl.
G03C 1/73 (2006.01)
G03F 7/039 (2006.01)
G03F 7/30 (2006.01)
C07C 43/15 (2006.01)
C08F 16/24 (2006.01)

(52) U.S. Cl. .................. 430/270.1; 430/326; 430/330; 430/907; 430/910; 568/591; 568/592; 568/594; 568/596; 568/599; 568/604; 526/247; 526/280; 526/281; 526/332

(58) Field of Classification Search ...................... None
See application file for complete search history.

(56) References Cited

U.S. PATENT DOCUMENTS 6,830,870 B2 * 12/2004 Malik et al. ............. 430/270.1

2003/0059710 A1 * 3/2003 Inoue ....................... 430/270.1

FOREIGN PATENT DOCUMENTS

| FR | 2.178.724 | 4/1972 |
| JP | 50-143888 | 11/1975 |
| JP | 2002-201219 | 7/2002 |

OTHER PUBLICATIONS

Hrabak et al ("Preparation and Properties of 1-Ethoxy-2,2,2-Trifluoroethyl Esters of Acrylic and Methacrylic Acids and of Their Polymers", Journal of Polymer Science: Part A: Polymer Chemistry, vol. 26, p. 267-274 (1988).*

* cited by examiner

Primary Examiner—Sin Lee
(74) Attorney, Agent, or Firm—Hayes Soloway P.C.

(57) ABSTRACT

As a polymer exhibiting improved transparency which is suitable for a resist resin used in a chemical-amplification-type resist being applicable for photolithography using exposure light at 180 nm or shorter, this invention provides a polymer comprising a repeating unit resulting from polymerization of a monomer exhibiting a polymerization activity, wherein the monomer has a fluorine-containing acetal or ketal structure represented by general formula (1):

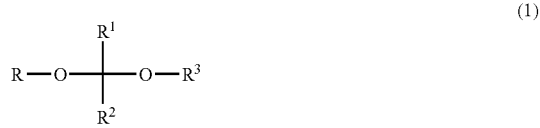

(1)

wherein

R represents an atomic group containing a carbon-carbon double bond exhibiting polymerization activity; at least one of $R^1$ and $R^2$ is fluorinated alkyl group or fluorinated aryl group having 1 to 20 carbon atoms; and $R^3$ represents a radical selected from the group consisting of hydrogen atom, alkyl group, alkoxy-substituted alkyl group, fluorinated alkyl group, aryl group, fluorinated aryl group, aralkyl group and fluorinated aralkyl group having 1 to 20 carbon atoms.

31 Claims, 1 Drawing Sheet

MONOMER HAVING FLUORINE-CONTAINING ACETAL OR KETAL STRUCTURE, POLYMER THEREOF, AND CHEMICAL-AMPLIFICATION-TYPE RESIST COMPOSITION AS WELL AS PROCESS FOR FORMATION OF PATTERN WITH USE OF THE SAME

TECHNICAL FIELD

This invention relates to a novel polymer resin having a fluorine-containing acetal or ketal structure in its side chain and a monomer having fluorine-containing acetal or ketal structure which is used for preparing the novel polymer resin; a chemical-amplification-type resist comprising the polymer; and a process for formation of pattern with use of the same. More specifically, it relates to a polymer compound useful as a component resin for a chemical-amplification-type resist, which is applicable in particular to formation of pattern employing far-ultraviolet light at a wavelength of 180 nm or shorter as exposure light thereto; and a monomer having a fluorine-containing acetal or ketal structure which is used for preparation of the polymer resin.

BACKGROUND ART

In the field of manufacturing a variety of electronic devices represented by a semiconductor device, fine processing technology in a half-micron level is requisite for completely meeting the requirements of further densification and integration of the device itself. Among others, requirements for photolithography usable for forming a fine pattern to allow for such fine processing has increasingly become more exacting. Specifically, in the case of manufacturing a DRAM with an integration degree of 1 G bits or higher, processing technology with a minimum line width of 0.13 µm or less is needed therefor. For complying with such rules, there has been employed photolithography using ArF excimer laser (193 nm) as exposure light. For the purpose of processing a further finer pattern, development in photolithography technology using $F_2$ excimer laser (157 nm) as exposure light has progressed recently [R. R. Kunz et al., Journal of Vacuum Science and Technology, Vol. B17(6), pp.3267–3272 (1999)].

Accordingly, there have been made, in parallel, progress in the development of resist materials adaptable to such photolithography using $F_2$ excimer laser (157 nm) as exposure light. As to performance required for a resist material fit to $F_2$ excimer laser exposure, in addition to a higher resolving potential answering such increased fineness in processing size, demand for higher sensitivity is on the rise. Specifically since a laser apparatus itself is expensive and a gas used as a laser medium has a short life in terms of $F_2$ excimer laser used for exposure, it is desired that a more sensitive resist material is used to minimize the quantity of exposure light required for each patterning process and thus to improve cost performance of the laser.

It is well known that a chemical-amplification-type resist with use of a photo-acid generator operating as a photosensitizer is one of hopeful approach for making a resist material more sensitive. Such approach as chemical-amplification-type resists have been also extensively used for a conventional resist material for KrF excimer laser exposure [e.g., Hiroshi Ito, C. Grant Wilson, American Chemical Society Symposium series, Vol, 242, pp.11–23 (1984)]. For example, in JP 2-27660 A1, disclosed is a chemical-amplification-type resist for which triphenylsulfonium hexafluoroarsenate is used as a photo-acid generator in combination with (p-tert-butoxycarbonyloxy-α-methylstyrene) as a resist resin. A characteristic feature of such chemical-amplification-type resist is that chemical amplification is achieved due to multiple acceleration of reaction in such a way that the photo-acid generator added as a photosensitizer component generates a proton acid in response to exposure light irradiation; and when heat-treating the resist post to the exposure step, one molecule of the proton acid generated by absorption of one photon induces and catalyzes an acid catalytic reactions of a resist resin or the like. A chemical-amplification-type resist utilizes said mechanism to realize drastically higher sensitivity in comparison with a conventional resist with a photoreaction efficiency (reaction per one photon) of less than 1. Currently, majority of resist materials being under development for excimer laser exposure belong to a chemical-amplification-type.

DISCLOSURE OF THE INVENTION

Furthermore, in the case of photolithography using light at a short wavelength of 180 nm or less represented by $F_2$ excimer laser beam as exposure light, a resist resin constituting a chemical-amplification-type resist for forming a fine pattern thereby is required to have a new property different from that in a resist resin material used in a chemical-amplification-type resist fit to conventional ArF excimer laser (193 nm) exposure, i.e., high transparency to exposure light at a wavelength of 180 nm or shorter.

In a photoresist fit to conventional KrF excimer laser (248 nm) or ArF excimer laser (193 nm) exposure, such a resin as poly(p-vinylphenol) or an alicyclic resin is mainly used as a resin component thereof. Whereas these resins show higher transparency at a wavelength of 190 nm or higher, their photoabsorptions to light at a wavelength of 180 nm or shorter are significantly strong. Therefore, if a conventional resin such as poly(p-vinylphenol) or an alicyclic resin is used in a chemical-amplification-type resist with aim to using light at a short wavelength of 180 nm or less as exposure light, a large part of the exposure light will be absorbed by the resist itself in the top surface of the resist layer, so that the exposure light fails to reach a substrate. Thus, a proton acid cannot be generated from a photo-acid generator used as a photosensitizer component over the whole resist film in its thickness direction, which causes failure of formation of a fine resist pattern. That is, a conventional resin itself, such as poly(p-vinylphenol) or an alicyclic resin, cannot be applied to a resin component constituting a chemical-amplification-type resist for photolithography using light at a shorter wavelength of 180 nm or less as exposure light. Accordingly, there has been strongly desired a novel resin material for a resist that exhibits higher transparency to light at a wavelength of 180 nm or shorter, which is applicable to a chemical-amplification-type resist for photolithography using light at a short wavelength of 180 nm or less as exposure light.

In order to solve the above problems, an objective of this invention is to provide a polymer that exhibits higher transparency to light at a wavelength of 180 nm or less and is useful as a resin material for a resist having acid-catalysis reactivity where a proton acid generated from a photo-acid generator in a photosensitizer component is involved as a catalyst, as well as a monomer used for preparation of said polymer. In addition, another objective of this invention is to provide a chemical-amplification-type resist comprising said polymer as a resin for a resist and a process for formation of pattern therewith.

For solving the above problems, we have intensely conducted studies and have finally obtained the following finding; it is essential that an atomic group constituting a principal chain in a polymer used as a resin material for a resist does not have significant absorption to light at a wavelength of 180 nm or less and 130 nm or more, and further an atomic group contained in a side chain in the polymer, which is involved in an acid-catalytic reaction by a proton acid generated from a photo-acid generator in a photo-sensitizer component, also does not have significant absorption to light at a wavelength of 180 nm or less and 130 nm or more. We have found that absorption of light at a wavelength of 180 nm or less and 130 nm or more can be significantly reduced as the whole polymer by selecting an atomic group having an acetal or ketal structure as said atomic group contained in the side chain of the polymer and further conducting fluorine substitution in the acetal or ketal structure thereof. In other words, we have verified that as for a monomer used for preparation of a polymer, a monomer having an atomic group involved in constituting the principal chain of the polymer and an acetal or ketal structure as for an atomic group to be a modifying group to the principal chain of the polymer is a useful monomer for preparing a desired polymer exhibiting higher transparency to light at a wavelength of 180 nm or less and 130 nm or more, and thus have achieved this invention.

That is to say, a monomer containing a carbon-carbon double bond exhibiting polymerization activity thereby and having a fluorine-containing acetal structure or ketal structure represented by general formula (1):

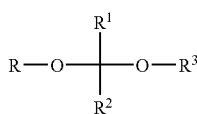

(1)

wherein

R represents an atomic group containing a carbon-carbon double bond exhibiting polymerization activity thereby;

$R^1$ and $R^2$ represent independently a radical selected from the group consisting of hydrogen atom, linear, branched or cyclic alkyl group, fluorinated alkyl group, aryl group and fluorinated aryl group having 1 to 20 carbon atoms and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms.

In this aspect, said monomer may be such type of the monomer characterized in that the atomic group represented by R has at least one skeletal structure selected from the group consisting of ethylene derivatives, vinyl chloride derivatives, styrene derivatives, acrylonitrile derivatives, (meth)acrylate derivatives, norbornene derivatives, ester derivatives of norbornenecaroboxylic acid, tetracyclododecene derivatives, ester derivatives of tetracyclododecenecarboxylic acid, tricyclononene derivatives and ester derivatives of tricyclononenecarboxylic acid.

Embodiments of the monomer compound according to this invention may include a monomer characterized in that the monomer is a (meth)acrylate derivative having a fluorine-containing acetal or ketal structure represented by general formula (2):

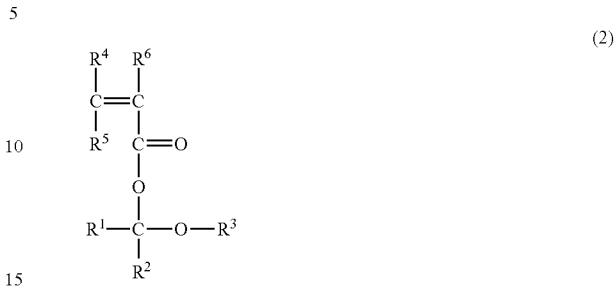

(2)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group.

Embodiments of the monomer compound according to this invention may include a monomer characterized in that the monomer is a norbornene derivative or tetracyclododecene derivative having a fluorine-containing acetal or ketal structure represented by general formula (3):

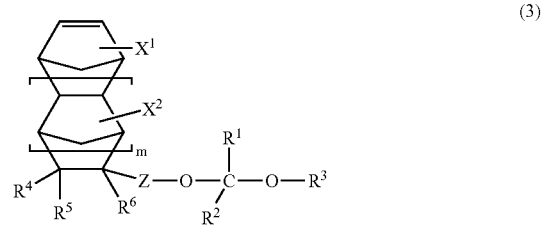

(3)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is the fluorinated alkyl group or the fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represents hydrogen atom or fluorine atom;

$R^6$ represents hydrogen atom, fluorine atom, methyl group or trifluoromethyl group;

$X^1$ and $X^2$ independently represent hydrogen atom or methyl group;

Z represents —CO—, methylene group or a linking group being composed of carbon-oxygen bond; and m is 0 or 1.

Embodiments of the monomer compound according to this invention may include a monomer characterized in that the monomer is a tricyclononene derivative having a fluorine-containing acetal or ketal structure represented by general formula (4):

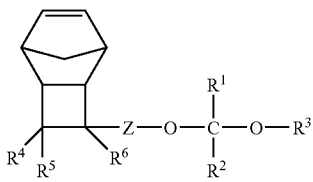

(4)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group;

Z represents —CO—, methylene group or a linking group composed of carbon-oxygen bond.

This invention also provides an invention of a polymer that can be prepared using the above monomer. Thus, an embodiment of the polymer according to this invention is a polymer being producible by polymerization of one or more monomer materials containing a carbon-carbon double bond exhibiting polymerization activity thereby, wherein the polymer comprises a repeating unit being obtainable by addition polymerization of at least one of the monomer having any one of such constitutions as defined above, as one of the repeating units contained in the polymer. Further embodiments of the polymer according to this invention include a polymer being producible by polymerization of one or more monomer materials containing a carbon-carbon double bond exhibiting polymerization activity thereby, wherein the polymer comprises a repeating unit being obtainable by ring-opening metathesis polymerization of at least one of the aforementioned monomer represented by general formula (3) or (4), as one of the repeating units contained in the polymer. In this case, the polymerization is followed by further treatment of hydrogenating a —CH=CH— moiety formed in the principal chain to convert into said repeating unit.

The polymer according to this invention described above may be used as a resist resin in a chemical-amplification-type resist composition. Accordingly, this invention also provides an invention of a chemical-amplification-type resist composition containing the polymer according to this invention as a resist resin. Thus, the chemical-amplification-type resist composition according to this invention is A resist composition of chemical-amplification-type comprising a resist resin and a photo-sensitizer therefor, wherein the composition comprises the polymer according to this invention as defined above.

Embodiments of the polymer according to this invention may include a polymer comprising one or more repeating units being obtainable by polymerization of a monomer containing a carbon-carbon double bond exhibiting polymerization activity thereby, wherein the unit has a fluorine-containing acetal or ketal structure represented by general formula (1a):

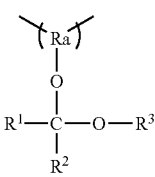

(1a)

wherein $R_a$ represents an atomic group being derived from an atomic group containing a carbon-carbon double bond exhibiting polymerization activity thereby and having linkages for composing a principal chain that are presented by polymerization;

$R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms.

In this aspect, said embodiments of the polymer according to this invention may be such type of the polymer characterized in that said repeating unit represented by general formula (1a) comprised in said polymer, the atomic group represented by $R_a$ is an atomic group having linkages for composing a principal chain that are presented by vinyl polymerization or ring-opening metathesis polymerization, and being derived from an atomic group having one or more skeletal structures selected from the group consisting of ethylene derivatives, vinyl chloride derivatives, styrene derivatives, acrylonitrile derivatives, (meth)acrylate derivatives, norbornene derivatives, norbornene carboxylic acid ester derivatives of norbornenecarboxylic acid, tetracyclododecene derivatives, ester derivatives of tetracyclododecene carboxylic acid, tricyclononene derivatives and ester derivatives of tricyclononene carboxylic acid.

Embodiments of the polymer according to this invention may include a polymer comprising one or more repeating units being obtainable by addition polymerization of a (meth)acrylate derivative, wherein the unit has a fluorine-containing acetal or ketal structure represented by general formula (2a):

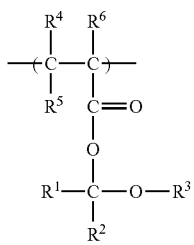

(2a)

wherein

R¹ and R² independently represent a radical selected from the group consisting of hydrogen atom, linear, branched or cyclic alkyl group, fluorinated alkyl group, aryl group and fluorinated aryl group having 1 to 20 carbon atoms; and at least one of R¹ and R² is said fluorinated alkyl group or fluorinated aryl group;

R³ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

R⁴ and R⁵ independently represent hydrogen atom or fluorine atom;

R⁶ represents hydrogen atom, fluorine atom, methyl group or trifluoromethyl group.

Embodiments of the polymer according to this invention may include a polymer comprising one or more repeating units being obtainable by addition polymerization of a norbornene derivative or tetracyclododecene derivative, wherein the unit has a fluorine-containing acetal or ketal structure represented by general formula (3a):

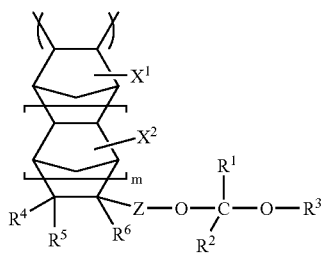

(3a)

wherein

R¹ and R² independently represent a radical selected from the group consisting of hydrogen atom, linear, branched or cyclic alkyl group, fluorinated alkyl group, aryl group and fluorinated aryl group having 1 to 20 carbon atoms; and at least one of R¹ and R² is said fluorinated alkyl group or fluorinated aryl group;

R³ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

R⁴ and R⁵ independently represent hydrogen atom or fluorine atom;

R⁶ represents hydrogen atom, fluorine atom, methyl group or trifluoromethyl group;

X¹ and X² independently represent hydrogen atom or methyl group;

Z represents —CO—, methylene group or a linking group composed of carbon-oxygen bond; and m is 0 or 1.

Embodiments of the polymer according to this invention may include a polymer comprising one or more repeating units being obtainable by addition polymerization of a tricyclononene derivative, wherein the unit has a fluorine-containing acetal or ketal structure represented by general formula (4a):

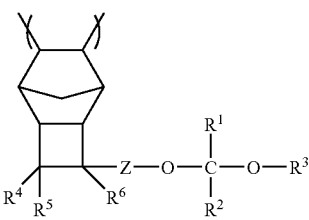

(4a)

wherein

R¹ and R² independently represent a radical selected from the group consisting of hydrogen atom, linear, branched or cyclic alkyl group, fluorinated alkyl group, aryl group and fluorinated aryl group having 1 to 20 carbon atoms; and at least one of R¹ and R² is said fluorinated alkyl group or fluorinated aryl group;

R³ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

R⁴ and R⁵ independently represent hydrogen atom or fluorine atom;

R⁶ represents hydrogen atom, fluorine atom, methyl group or trifluoromethyl group;

Z represents —CO—, methylene group or a linking group composed of carbon-oxygen bond.

Embodiments of the polymer according to this invention may include a polymer comprising one or more repeating units being obtainable by ring-opening polymerization of a norbornene derivative or tetracyclododecene derivative and then hydrogenating a —CH═CH— moiety resulting therefrom, wherein the unit has a fluorine-containing acetal or ketal structure represented by general formula (3b):

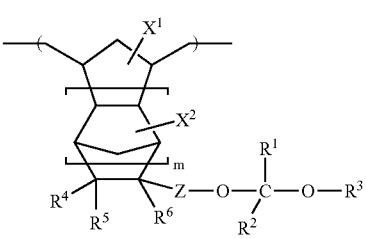

(3b)

wherein

R¹ and R² independently represent a radical selected from the group consisting of hydrogen atom, linear, branched or cyclic alkyl group, fluorinated alkyl group, aryl group and fluorinated aryl group having 1 to 20 carbon atoms; and at least one of R¹ and R² is said fluorinated alkyl group or fluorinated aryl group;

R³ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group;

$X^1$ and $X^2$ independently represent hydrogen atom or methyl group;

Z represents —CO—, methylene group or a linking group composed of carbon-oxygen bond; and m is 0 or 1.

Embodiments of the polymer according to this invention may include a polymer comprising one or more repeating units being obtainable by ring-opening polymerization of a tricyclononene derivative and then hydrogenating a —CH═CH— moiety resulting therefrom, wherein the unit has a fluorine-containing acetal or ketal structure represented by general formula (4b):

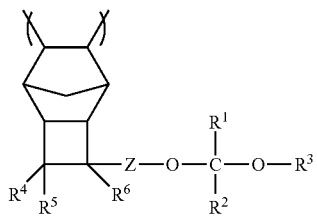

(4b)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group;

Z represents —CO—, methylene group or a linking group composed of carbon-oxygen bond.

Furthermore, in the case of said polymers according to this invention, the polymer may be such type of the polymer characterized in that the polymer comprises, in addition to said repeating unit having a fluorine-containing acetal or ketal structure represented by general formula (2a), (3a), (4a), (3b) or (4b), one or more repeating units selected from the group consisting of a repeating unit represented by general formula (5):

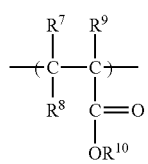

(5)

wherein $R^7$ and $R^8$ are independently hydrogen atom or fluorine atom;

$R^9$ is hydrogen atom, fluorine atom, methyl group or trifluoromethyl group;

$R^{10}$ represents a radical selected from the group consisting of hydrogen atom; linear, branched or cyclic alkyl group and fluorinated alkyl group having 1 to 20 carbon atoms; a group removable by an acid; a bridged cyclic hydrocarbon group having 7 to 13 carbon atoms containing a group removable by an acid thereon and norbornane-2,6-carbolactone-5-yl group;

a repeating unit represented by general formula (6):

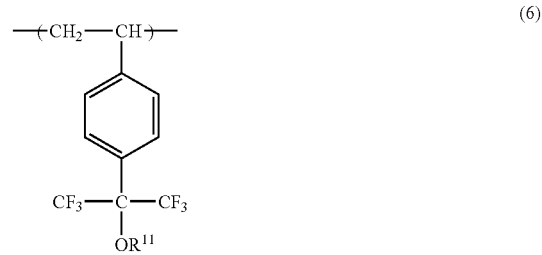

(6)

wherein $R^{11}$ represents hydrogen atom or a group removable by an acid;

a repeating unit represented by general formula (7):

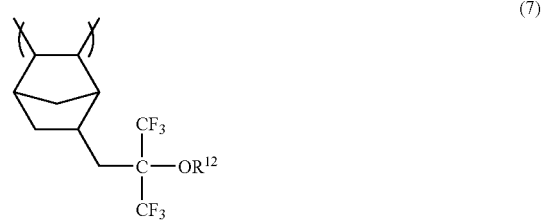

(7)

wherein $R^{12}$ represents hydrogen atom or a group removable by an acid;

a tetrafluoroethylene radical represented by formula (8):

—CF$_2$—CF$_2$— (8)

a repeating unit represented by general formula (9):

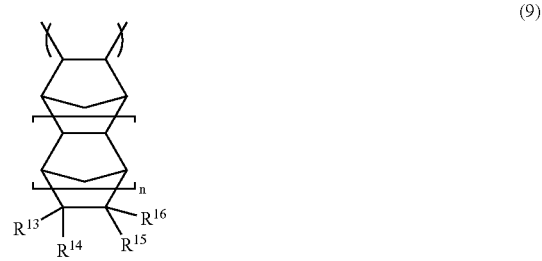

(9)

wherein $R^{13}$ and $R^{14}$ independently represent hydrogen atom or fluorine atom; $R^{15}$ represents hydrogen atom, fluorine atom, methyl group or trifluoromethyl group; $R^{16}$ represents hydrogen atom, hydroxy group, hydroxy alkyl group or an acid-dissociable organic group having 20 or less carbon atoms which can generate a carboxy group therefrom by its decomposition by an acid;

a repeating unit represented by general formula (10):

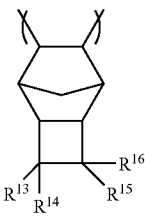

(10)

wherein $R^{13}$ and $R^{14}$ independently represent hydrogen atom or fluorine atom; $R^{15}$ represents hydrogen atom, fluorine atom, methyl group or trifluoromethyl group; $R^{16}$ represents hydrogen atom, hydroxy group, hydroxy alkyl group or an acid-dissociable organic group having 20 or less carbon atoms which can generate a carboxy group therefrom by its decomposition by an acid;

a repeating unit represented by general formula (11):

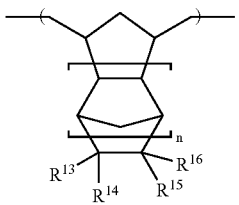

(11)

wherein $R^{13}$ and $R^{14}$ are independently hydrogen atom or fluorine atom; $R^{15}$ represents hydrogen atom, fluorine atom, methyl group or trifluoromethyl group; $R^{16}$ represents hydrogen atom, hydroxy group, hydroxy alkyl group or an acid-dissociable organic group having 20 or less carbon atoms which can generate a carboxy group therefrom by its decomposition by an acid;

a repeating unit represented by general formula (12):

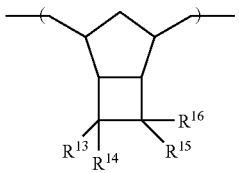

(12)

wherein $R^{13}$ and $R^{14}$ are independently hydrogen atom or fluorine atom; $R^{15}$ represents hydrogen atom, fluorine atom, methyl group or trifluoromethyl group; $R^{16}$ represents hydrogen atom, hydroxy group, hydroxy alkyl group or an acid-dissociable organic group having 20 or less carbon atoms which can generate a carboxy group therefrom by its decomposition by an acid; and anhydrous succindiyl (tetrahydrofuran-2,5-dion-3,4-diyl) represented by formula (13):

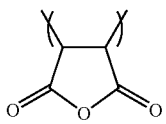

(13)

Additionally, the polymers according to this invention may be constituted in such manner that the polymer comprises said repeating unit represented by any one of general formulas (2a), (3a), (3b), (4a) and (4b) in a content of at least 5 to 90 mol % to the total number of the repeating units composing the polymer.

In the light of the use as a resist resin, it is preferred that the polymer according to this invention may be a polymer characterized in that a weight-average molecular weight of the polymer is selected in the range of 2,000 to 200,000.

On the other hand, a resist composition of chemical-amplification type according to this invention is preferably a resist composition of chemical-amplification-type comprising a resist resin and a photo-sensitizer, wherein the composition comprises one or more of the polymers of this invention having any one of the constitutions as defined above as said resist resin and at least a photo-acid generator capable of generating an acid by exposure light as said photo-sensitizer; and the content of the photo-acid generator to the total amount of the polymer and the photo-acid generator is selected in the range of 0.2 to 30 wt %.

Furthermore, this invention also provides a process for formation of pattern by photolithography utilizing a resist composition of chemical-amplification-type according to this invention. Specifically, the process for formation of pattern of this invention is defined as a process for formation of pattern by photolithography utilizing a chemical-amplification-type resist, comprising at least the steps of:

forming a film of the aforementioned chemical-amplification-type resist of this invention applied onto a substrate to be processed for formation of pattern thereon;

irradiating the substrate with light at a wavelength of 130 to 180 nm as exposure light in accordance with a pattern to be formed to expose said film of the chemical-amplification-type resist;

carrying out baking treatment for said exposed film of the chemical-amplification-type resist;

carrying out developing treatment for said film treated by baking. For instance, in the process for formation of pattern according to this invention, $F_2$ excimer laser beam may be suitably employed for the light at a wavelength of 130 to 180 nm used in said exposure step. In other words, the polymer of this invention comprises fluorine atoms so that it can attain adequate transparency to light at 180 nm or shorter.

BEST MODE FOR CARRYING OUT THE INVENTION

Figure 1:
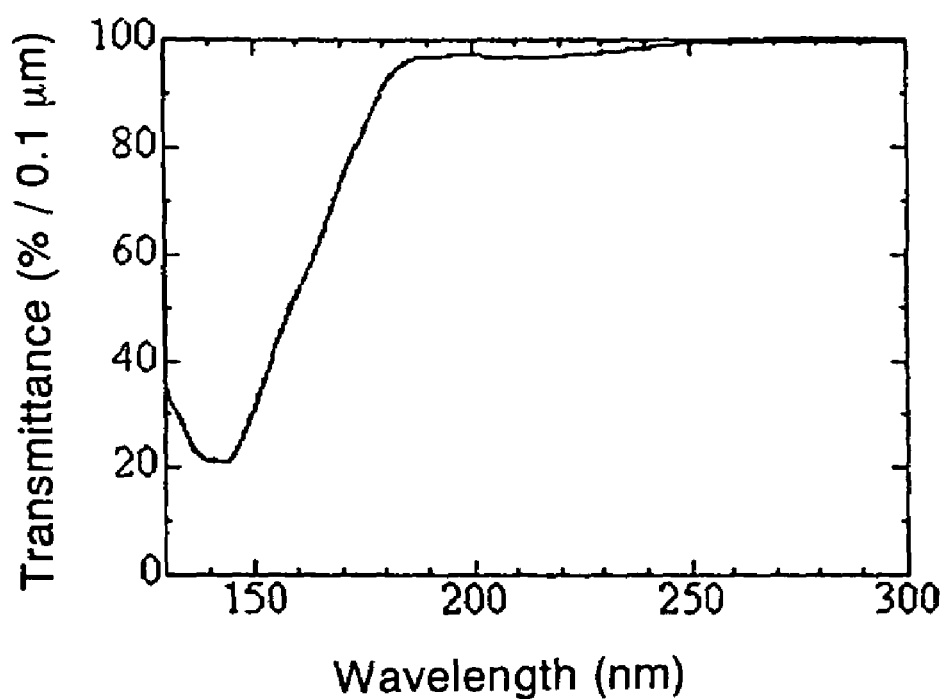
FIG. 1 is a graph showing a light transmittance curve in an ultraviolet range observed for the coating film of the polymer resin obtained in Example 12.

This invention will be explained hereafter in detail.

In a monomer compound according to this invention, i.e., a monomer containing a carbon-carbon double bond exhibiting polymerization activity thereby and having a fluorine-containing acetal structure or ketal structure represented by general formula (1), the atomic group R containing a carbon-carbon double bond exhibiting polymerization activity thereby may be, without limitations, any of those which exhibit adequate polymerization activity and after polymerization can form a principal chain to give a polymer for a chemical-amplification-type resist with good properties. Among those, in the light of obtaining a polymer for a chemical-amplification-type resist possessing an adequate molecular weight and transparency at an exposure light wavelength, it is preferable to employ an atomic group having one or more skeletal structures selected from the group consisting of ethylene derivatives, vinyl chloride derivatives, styrene derivatives, acrylonitrile derivatives, (meth)acrylate derivatives, norbornene derivatives, ester derivatives of norbornenecaroboxylic acid, tetracyclododecene derivatives, ester derivatives of tetracyclododecenecarboxylic acid, tricyclononene derivatives and ester derivatives of tricyclononenecarboxylic acid. For instance, a polymer prepared by addition polymerization or ring-opening metathesis polymerization using a monomer employing said atomic group having the skeletal structure as the atomic group R containing a carbon-carbon double bond exhibiting polymerization activity thereby consequently comprises in its principal chain a repeating unit obtainable by addition polymerization or addition polymerization of the carbon-carbon double bond that is present in these skeletal structure such as ethylene derivatives, vinyl chloride derivatives, styrene derivatives, acrylonitrile derivatives, (meth)acrylate derivatives, norbornene derivatives, ester derivatives of norbornenecaroboxylic acid, tetracyclododecene derivatives, ester derivatives of tetracyclododecenecarboxylic acid, tricyclononene derivatives and ester derivatives of tricyclononenecarboxylic acid.

In particular, suitable examples of a monomer in which an atomic group R contains an addition-polymerizable carbon-carbon double bond may include a (meth)acrylate derivative having a fluorine-containing acetal or ketal structure represented by general formula (2):

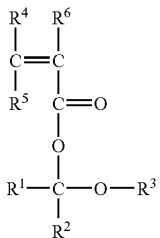

(2)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group. Such a (meth)acrylate derivative of general formula (2) can be subjected to addition polymerization to obtain a polymer corresponding thereto which comprises a repeating unit represented by general formula (2a):

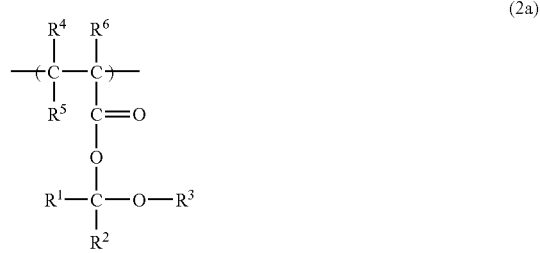

wherein $R^1$, $R^2$, $R^4$, $R^5$ and $R^6$ represent the same radicals as $R^1$, $R^2$, $R^4$, $R^5$, $R^6$ defined in general formula (2), respectively.

Furthermore, suitable examples of monomer having a bridged ring frame that involves a norbornene-ring structure containing an endocyclic carbon-carbon double bond, which is ring-opening-polymerizable as well as addition-polymerizable, in the atomic group R thereof may include a norbornene derivative or tetracyclo[4.4.0.1$^{2,5}$.1$^{7,10}$]-3-dodecene derivative having a fluorine-containing acetal or ketal structure represented by general formula (3):

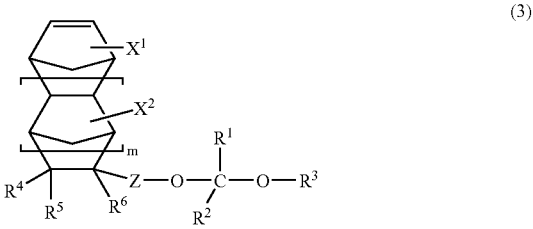

wherein $R^1$ and $R^2$ independently represent a radical selected from the group consisting of hydrogen atom, linear, branched or cyclic alkyl group, fluorinated alkyl-group, aryl group and fluorinated aryl group having 1 to 20 carbon atoms; and at least one of $R^1$ and $R^2$ is the fluorinated alkyl group or the fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group;

$X^1$ and $X^2$ independently represent hydrogen atom or methyl group;

Z represents —CO—, methylene group or a linking group being composed of carbon-oxygen bond; and m is 0 or 1. Such a norbornene derivative or tetracyclododecene derivative of general formula (3) can be subjected to addition polymerization to obtain a polymer corresponding thereto which comprises a repeating unit represented by general formula (3a):

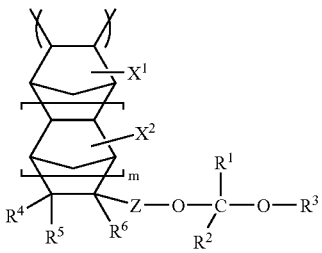

(3a)

wherein $R^1$, $R^2$, $R^4$, $R^5$, $R^6$, $X^1$, $X^2$ and Z represent the same as $R^1$, $R^2$, $R^4$, $R^5$, $R^6$, $X^1$, $X^2$ and Z defined in general formula (3), respectively; and m is an identical integer to that defined for m in general formula (3). On the other hand, the norbornene derivative or tetracyclododecene derivative of general formula (3) can be subjected to ring-opening metathesis polymerization followed by hydrogenation of a —CH=CH— moiety resulting therefrom to obtain a polymer corresponding thereto which comprises a repeating unit represented by general formula (3b):

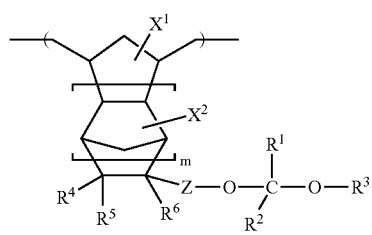

(3b)

wherein $R^1$, $R^2$, $R^4$, $R^5$, $R^6$, $X^1$, $X^2$ and Z represent the same radicals as $R^1$, $R^2$, $R^4$, $R^5$, $R^6$, $X^1$, $X^2$ and Z defined in general formula (3), respectively; and m is an identical integer to that defined for m in general formula (3).

In addition, suitable examples of monomer having a bridged ring frame that involves a norbornene-ring structure containing an endocyclic carbon-carbon double bond, which is ring-opening-polymerizable as well as addition-polymerizable, in the atomic group R thereof may include a tricyclo [4.2.1.0$^{2,5}$]-7-nonene derivative having a fluorine-containing acetal or ketal structure represented by general formula (4):

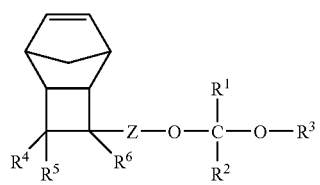

(4)

wherein $R^1$ and $R^2$ independently represent a radical selected from the group consisting of hydrogen atom, linear, branched or cyclic alkyl group, fluorinated alkyl group, aryl group and fluorinated aryl group having 1 to 20 carbon atoms; and at least one of $R^1$ and $R^2$ is said fluorinated alkyl group or fluorinated aryl group;

$R^3$ represents a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms;

$R^4$ and $R^5$ independently represent hydrogen atom or fluorine atom;

$R^6$ represents hydrogen atom, fluorine atom, methyl group or trifluoromethyl group;

Z represents —CO—, methylene group or a linking group composed of carbon-oxygen bond. Such a tricyclononene derivative of general formula (4) can be subjected to vinyl polymerization to obtain a polymer corresponding thereto which comprises a repeating unit represented by general formula (4a):

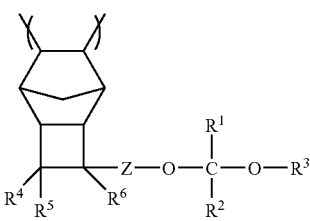

(4a)

wherein $R^1$, $R^2$, $R^4$, $R^5$, $R^6$ and Z represent the same radicals as $R^1$, $R^2$, $R^4$, $R^5$, $R^6$ and Z defined in general formula (4), respectively. On the other hand, the tricyclononene derivative of general formula (4) may be subjected to ring-opening metathesis polymerization followed by hydrogenation of a —CH=CH— moiety resulting therefrom to obtain a polymer corresponding thereto which comprises a repeating unit represented by general formula (4b):

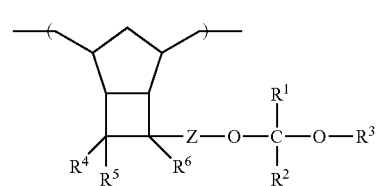

(4b)

wherein $R^1$, $R^2$, $R^4$, $R^5$, $R^6$ and Z represent the same radicals as $R^1$, $R^2$, $R^4$, $R^5$, $R^6$ and Z defined in general formula (4), respectively.

Although the polymer according to this invention is the aforementioned polymer comprising a repeating unit derived from the monomer represented by general formula (1), it may be, if necessary, a copolymer comprising two or more repeating units. Accordingly, two or more monomers having different structures can be copolymerized to prepare a copolymer having two or more repeating units in a principal chain, and in a chemical-amplification-type resist according to this invention, such a copolymer can be used as a resist resin to provide a resist obtained with a wider variety of properties.

Furthermore, in said monomer represented by general formula (1), (2), (3) or (4) and said repeating unit represented by general formula (1a), (2a), (3a), (3b), (4a) or (4b) derived from these monomers, suitable groups for radicals $R^1$, $R^2$ and $R^3$ being components involved in the fluorine-containing acetal or ketal structure may include those exemplified as follows. The radicals $R^1$ and $R^2$ are independently a radical selected from the group consisting of hydrogen atom, linear, branched or cyclic alkyl group, fluorinated alkyl group, aryl group and fluorinated aryl group having 1 to 20 carbon atoms. More specific examples of such a suitable linear, branched or cyclic alkyl group having 1 to 20 carbon atoms may include such a group as methyl, ethyl, propyl, isopropyl, butyl, isobutyl, sec-butyl, tert-butyl, pentyl, hexyl, cyclohexyl, norbornyl, adamanthyl, tricyclodecyl and tetracyclododecyl groups. Thus, the fluorinated alkyl group having 1 to 20 carbon atoms is a fluorinated derivative of the linear, branched or cyclic alkyl group described above. More specific examples of such a suitable fluorinated alkyl group may include such a group as fluoromethyl, fluoroethyl, difluoromethyl, trifluoromethyl, trifluoroethyl, tetrafluoroethyl and pentafluoroethyl groups. On the other hand, the aryl group as used herein may include an aromatic group with up to 20 carbon atoms in total, which aromatic ring is optionally substituted with alkyl group(s) or the like. More specifically, suitable examples of such an aryl group may include such a group as phenyl, tolyl and naphthyl groups. The fluorinated aryl group is such a group that has substitution with fluorine(s) on said aryl group with up to 20 carbon atoms in total. More particularly, preferable examples of such a fluorinated aryl group may include such a group as difluorophenyl, trifluorophenyl and pentafluorophenyl groups. Additionally, at least one of radicals $R^1$ and $R^2$ may be selected from the fluorinated alkyl group or fluorinated aryl group described above to give a fluorine-containing acetal or ketal structure.

On the other hand, the radical $R^3$ is a radical selected from the group consisting of hydrogen atom, linear, branched or cyclic alkyl group, alkoxy-substituted alkyl group, fluorinated alkyl group, aryl group, fluorinated aryl group, aralkyl group and fluorinated aralkyl group having 1 to 20 carbon atoms. More specific examples of a suitable linear, branched or cyclic alkyl group having 1 to 20 carbon atoms may include such a group as methyl, ethyl, n-propyl, isopropyl, butyl, isobutyl, sec-butyl, tert-butyl, cyclohexyl, cyclohexylmethyl, norbornyl, norbornylmethyl, adamanthyl, adamanthylmethyl, tricyclodecyl, tricyclodecylmethyl, tetracyclododecyl and tetracyclododecylmethyl groups. Thus, the fluorinated alkyl group having 1 to 20 carbon atoms is a fluorinated derivative of the linear, branched or cyclic alkyl group described above. More particularly, suitable examples of the fluorinated alkyl group may include such a group as 2-fluoroethyl, fluorooctyl, trifluoroethyl and pentafluoropropyl groups. The alkoxy-substituted alkyl group is an alkoxy-substituted derivative of the alkyl group described above having 1 to 20 carbon atoms. The total number of skeletal atoms in the whole molecule of the alkoxy-substituted alkyl group is preferably chosen within 20 or less. More specific examples of such a preferable alkoxy-substituted alkyl group may include such a group as methoxyethyl, ethoxyethyl, ethoxypropyl and methoxypropyl groups.

On the other hand, the aryl group for the radical $R^3$ may include an aromatic group with up to 20 carbon atoms in total, which aromatic ring is optionally substituted with alkyl group(s) or the like. More specific examples of such an aryl group may include such a group as phenyl, tolyl and naphthyl groups. The fluorinated aryl group is such a group that has substitution with fluorine(s) on said aryl group with up to 20 carbon atoms in total. More particularly, preferable examples of the fluorinated aryl group may include such a group as difluorophenyl and pentafluorophenyl groups. Furthermore, the aralkyl group is such a group that is an alkyl group substituted by said aryl group with up to 20 carbon atoms in total. The total number of skeletal carbon atoms in the whole molecule of the aralkyl group is preferably chosen within 20 or less. More specifically, examples of the preferable aralkyl group may include such a group as benzyl and phenethyl groups. The fluorinated aralkyl group may be typically a derivative of the aralkyl group in which the aryl group moiety is, for example, substituted with fluorine. More particularly, preferable examples of the fluorinated aralkyl group may include such a group as difluorobenzyl and pentafluorobenzyl groups.

As for the radicals $R^4$, $R^5$ and $R^6$ which are present as substituents in a skeletal structure constituting a principal chain after polymerization, in the monomer represented by general formula (2), (3) or (4) as well as the repeating unit derived from the monomer represented by general formula (2a), (3a), (3b), (4a) or (4b), the radicals $R^4$ and $R^5$ may be independently selected from hydrogen or fluorine atoms while the radical $R^6$ may be chosen form hydrogen atom, fluorine atom, methyl group or trifluoromethyl group.

Furthermore, among the aforementioned (meth)acrylate derivatives having a fluorine-containing acetal or ketal structure represented by general formula (2), examples of a more preferable compound may include a group of the compounds listed below.

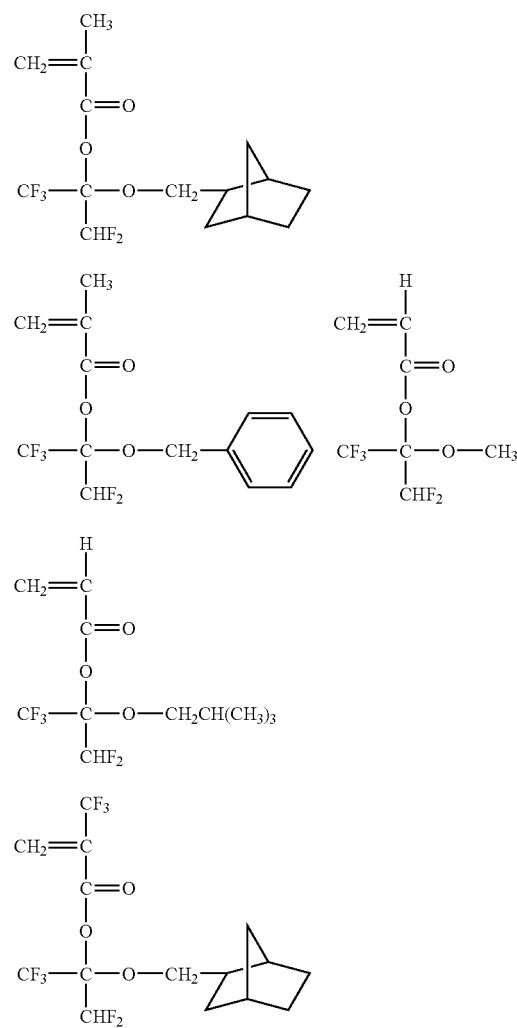

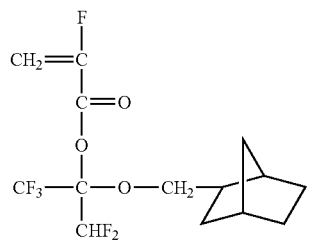
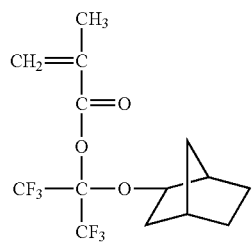
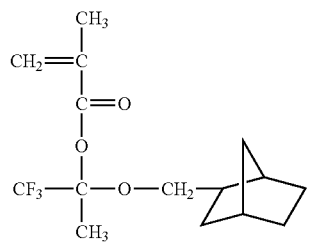
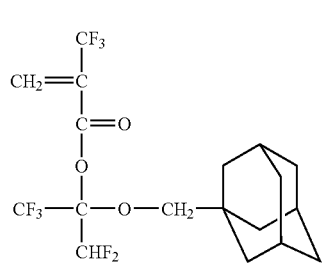
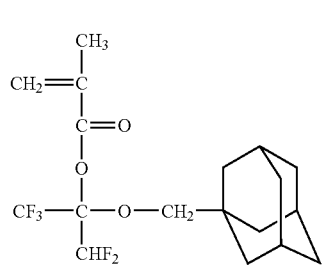
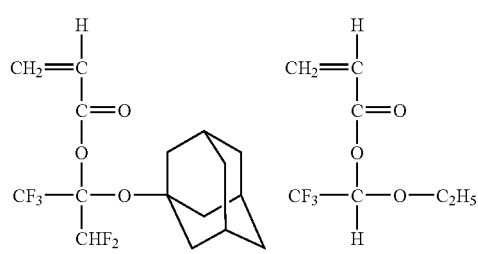
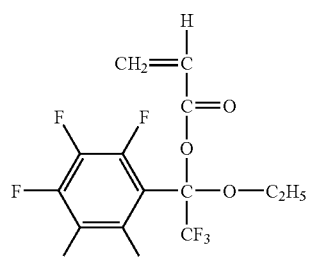
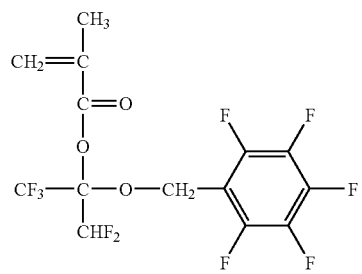
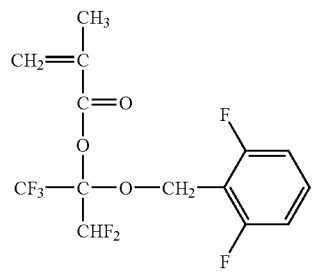
Among the aforementioned norbornene derivatives or tetracyclododecene derivatives having a fluorine-containing acetal or ketal structure represented by general formula (3), examples of a more preferable compound may include a group of the compounds listed below.
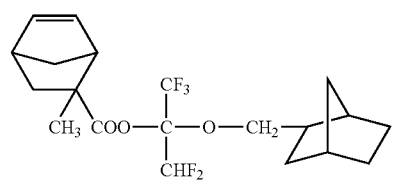
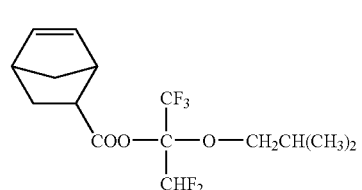
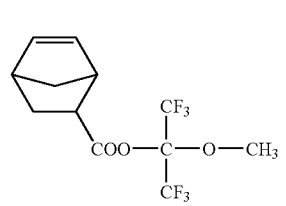

-continued
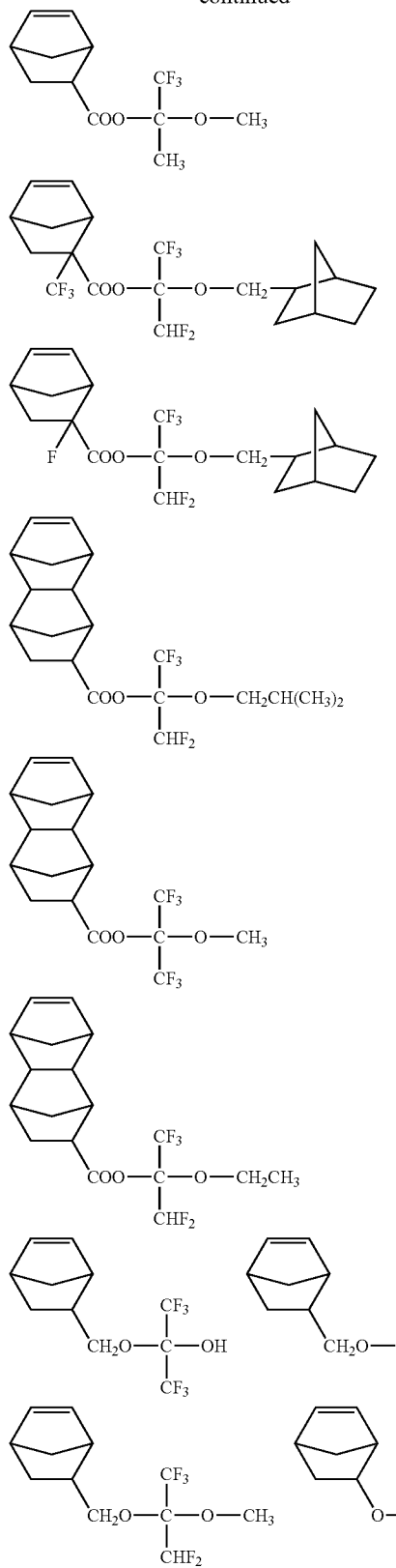
On the other hand, among the aforementioned tricyclononene derivatives having a fluorine-containing acetal or ketal structure represented by general formula (4), examples of a more preferable compound may include a group of the compounds summarized below.
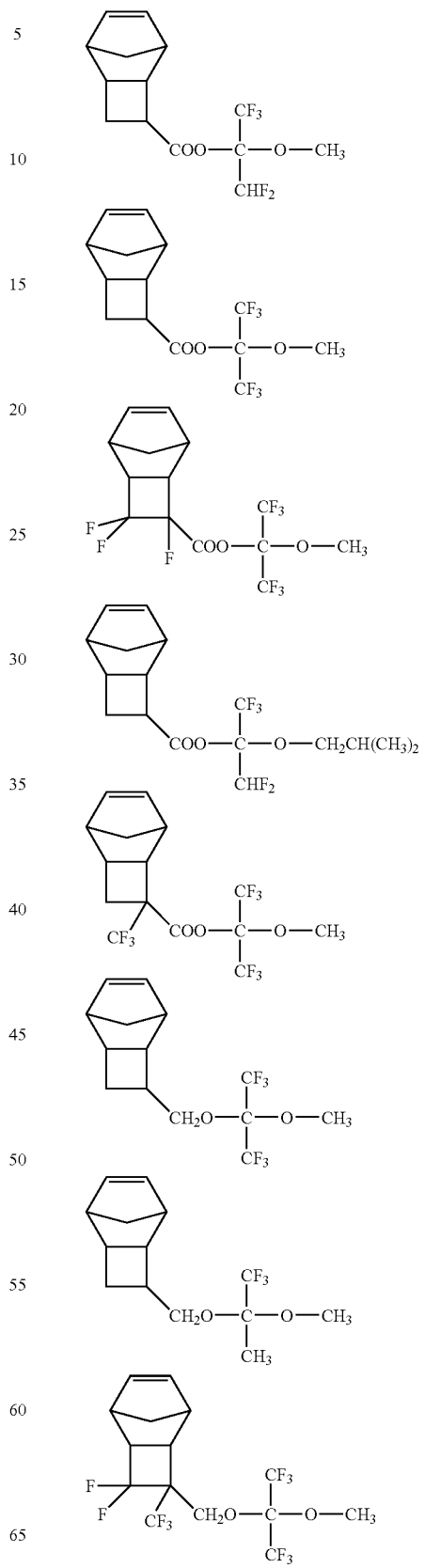

Furthermore, the polymer according to this invention may be a copolymer comprising another repeating unit which may provide aimed properties of a polymer for a chemical-amplification-type resist, in addition to the repeating unit represented by general formula (1a), (2a), (3a), (3b), (4a) or (4b). For example, such an additional repeating unit may be suitably employed that whose corresponding monomer possesses adequate polymerization activity such that it can be readily copolymerized with the monomer represented by general formula (1), (2), (3) or (4). Suitable examples of such an additional repeating monomer whose corresponding monomer has adequate polymerization activity and may provide a resulted copolymer with aimed performance for a resist polymer for a chemical-amplification-type resist may include the repeating units represented by general formulas (5) to (7), formula (8), general formulas (9) to (12) and formula (13) illustrated above.

In the repeating unit represented by general formula (5):

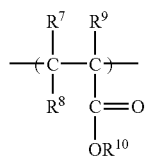

(5)

as for the substituents on the principal-chain frame, the radicals $R^7$ and $R^8$ are independently hydrogen atom or fluorine atom; and the radical $R^9$ is hydrogen atom, fluorine atom, methyl group or trifluoromethyl group. On the other hand, the radical $R^{10}$ as a substituent to the carboxy group therein may be a radical selected from the group consisting of hydrogen atom; linear, branched or cyclic alkyl group and fluorinated alkyl group having 1 to 20 carbon atoms; a group removable by an acid; a bridged cyclic hydrocarbon group having 7 to 13 carbon atoms containing a group removable by an acid thereon and norbornane-2,6-carbolactone-5-yl group. More specifically, suitable examples of the linear, branched or cyclic alkyl group having 1 to 20 carbon atoms may include, but not limited to, such a group as methyl, ethyl, propyl, isopropyl, butyl, isobutyl, sec-butyl, pentyl, cyclohexyl, norbornyl, isobornyl, adamanthyl and tricyclodecyl groups. The fluorinated alkyl group is a fluorinated derivative of said linear, branched or cyclic alkyl group. More particularly, preferable examples of the fluorinated alkyl group may include, but not limited to, such a group as fluoromethyl, fluoroethyl, fluoropropyl, difluoromethyl, trifluoromethyl, tetrafluoroethyl, pentafluoroethyl, hexafluoroisopropyl and nonafluorohexyl group. The group removable by an acid means a group which can be removed by an acid-catalytic reaction for regaining carboxy group. More specifically, suitable examples thereof may include, but not limited to, such a group as tert-butyl, tetrahydropyran-2-yl, tetrahydrofuran-2-yl, 4-methoxytetrahydropyran-4-yl, 1-ethoxyethyl, 1-butoxyethyl, 1-propoxyethyl, 3-oxocyclohexyl, 2-methyl-2-adamanthyl, 2-ethyl-2-adamanthyl, 1-methyl-1-adamanthylethyl, 8-methyl-8-tricyclo[5.2.1.0$^{2,6}$]decyl, 1,2,7,7-tetramethyl-2-norbornyl, 2-acetoxymenthyl, 2-hydroxymenthyl and 1-methyl-1-cyclohexylethyl groups. Specific examples of the bridged cyclic hydrocarbon group with 7 to 13 carbon atoms containing the group removable by an acid may include, but not limited to, such a bridged cyclic hydrocarbon group with 7 to 13 carbon atoms containing a group removable by an acid as described in JP 2,856,116 B1. Similarly,. norbornane-2,6-carbolactone-5-yl group, which comprises an endocyclic lactone ring therein may be also employed for the radical $R^9$.

In the repeating unit represented by general formula (6):

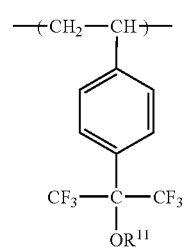

(6)

the radical $R^{11}$ used therein is hydrogen atom or a group removable by an acid. Specific examples of a group removable by an acid, which is suitable for the radical $R^{11}$, may include, but not limited to, such a group as tert-butyl, tert-butoxycarbonyl, methoxymethyl, ethoxyethyl, tetrahydropyranyl and tetrahydrofuranyl groups.

Furthermore, in the repeating unit represented by general formula (7):

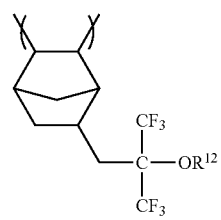

(7)

the radical $R^{12}$ used therein is hydrogen atom or a group removable by an acid. Specific examples of a group removable by an acid, which is suitable for the radical $R^{12}$, may include, but not limited to, such a group as tert-butyl, tert-butoxycarbonyl, methoxymethyl, ethoxyethyl, tetrahydropyranyl and tetrahydrofuranyl groups.

On the other hand, the repeating unit represented by general formula (9):

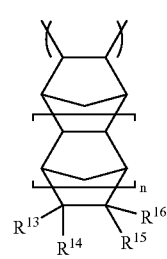

(9)

or the repeating unit represented by general formula (11):

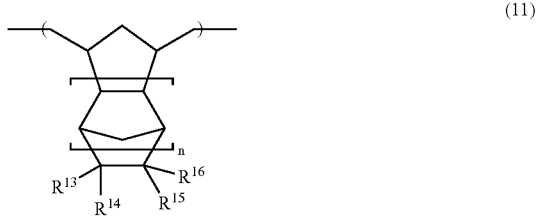

(11)

is a repeating unit derived from a monomer corresponding thereto, which has, for instance, a norbornene structure in the case where n is 0 or tetracyclododecene structure in the case where n is 1, wherein it can be obtained by conducting addition polymerization or ring-opening metathesis polymerization of the monomer, respectively and then hydrogenating a resulting —CH═CH— moiety.

Similarly, the repeating unit represented by general formula (10):

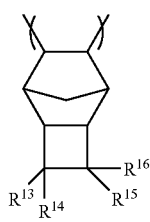

(10)

or the repeating unit represented by general formula (12):

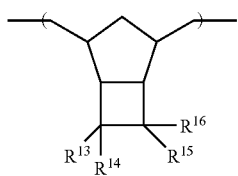

(12)

is a repeating unit derived from a monomer corresponding thereto, which has a tricyclononene structure, wherein it can be obtained by conducting addition polymerization or ring-opening metathesis polymerization of the monomer, respectively and then hydrogenating a resulting —CH═CH— moiety.

As for the radicals $R^{13}$, $R^{14}$, $R^{15}$, $R^{16}$ as substituents on the polycyclic structures in said repeating units represented by general formulas (9) or (11) and general formulas (10) or (12), the radicals $R^{13}$ and $R^{14}$ are independently selected from hydrogen atom or fluorine atom, and the radical $R^{15}$ is chosen from hydrogen atom, fluorine atom, methyl group or trifluoromethyl group, while the radical $R^{16}$ is selected from hydrogen atom, hydroxy group, hydroxyalkyl group and an acid-dissociable organic group having up to 20 carbon atoms which can generate a carboxy group therefrom by its decomposition by an acid. More specifically, suitable examples of the hydroxy alkyl group include, but not limited to, such a group as hydroxymethyl and hydroxyethyl group. On the other hand, the acid-dissociable organic group having up to 20 carbon atoms which can generate a carboxy group therefrom by its decomposition by an acid means, in particular, an ester type acid-dissociable organic group such as O-substituted carboxy type. Suitable examples thereof include, but not limited to, such a group as tert-butoxycarbonyl, tetrahydropyranyloxycarbonyl, tetrahydrofuranyloxycarbonyl, 4-methoxytetrahydropyranyloxycarbonyl, 1-ethoxyethoxycarbonyl, 1-butoxyethoxycarbonyl, 1-propoxyethoxycarbonyl, 3-oxocyclohexyloxycarbonyl, 2-methyl-2-adamanthyloxycarbonyl, 2-ethyl-2-adamanthyloxycarbonyl, 8-methyl-8-tricyclo[5.2.1.0$^{2,6}$]decyloxycarbonyl or 1,2,7,7-tetramethyl-2-norbornyloxycarbonyl, 2-acetoxymenthyloxycarbonyl, 2-hydroxymenthyloxycarbonyl and 1-methyl-1-cyclohexylethoxycarbonyl groups.

Besides, the tetrafluoroethylene repeating unit represented by formula (8):

(8)

is obtainable by addition polymerization of a corresponding monomer, and the anhydrous succindiyl (tetrahydrofuran-2,5-dion-3,4-diyl) represented by formula (13):

(13)

is obtainable by addition polymerization of a corresponding monomer, i.e. maleic anhydride.

The polymer according to this invention preferably comprises the repeating unit represented by general formula (2a), (3a), (3b), (4a) or (4b). In the light of performance of a polymer obtained, when forming a copolymer comprising an additional repeating unit together with them, the summed content of the repeating units represented by general formulas (2a), (3a), (3b), (4a) and (4b) in the total repeating units is desirably selected at least 5 mol % or more, preferably 7 mol % or more. On the other hand, in the light of polymer performance obtained, for allowing a content of the additional repeating unit combined to be generally adjusted to 10 mol % or more, preferably to 20 mol % or more to the whole repeating units, it is desirable to keep a summed proportion of the repeating units represented by general formulas (2a), (3a), (3b), (4a) and (4b) in total to the whole repeating units preferably within 90 mol % or less, more preferably within 80 mol % or less.

The polymer of this invention can be prepared by polymerizing the aforementioned monomer(s) used as starting materials by a conventional technique for polymerization such as radical polymerization, anionic polymerization, addition polymerization and ring-opening metathesis polymerization. For example, when employing radical polymerization, the reaction in dry tetrahydrofuran under an inert gas (e. g., argon or nitrogen) atmosphere can be conducted by adding an appropriate radical-polymerization initiator (for example, azobisbutyronitrile) and then stirring and heating at 50 to 70° C. for 0.5 to 12 hours to complete polymerization reaction.

Alternatively, when employing, for example, addition polymerization, the polymerization can be accelerated by using, as a catalyst, a palladium compound (for example, {(η$^3$-allyl)Pd(BF$_4$)}, {(η$^3$-allyl)Pd(SbF$_6$)}, [Pd(CH$_3$CN)$_4$][BF$_4$]$_2$ or etc.) in accordance with the method of J. P.

Mathew et al. disclosed in Macromolecules, Vol. 29, pp.2755–2763 (1996) or a nickel compound [bis(pentafluorophenyl)nickel-toluene complex] in accordance with the method of T. Chiba et al. disclosed in Journal of Photopolymer Science and Technology, Vol. 13 (4), pp.657–664 (2000).

Alternatively, when preparing a polymer by ring-opening metathesis polymerization, examples of a metathesis catalyst applicable thereto may include, but not limited to, halides of a transition metal such as W (tungsten), Mo (molybdenum) and Re (rhenium); more specifically, such as $WCl_6$, $MoCl_5$ and $ReCl_3$. Such a metathesis catalyst is used to initiate ring-opening polymerization and then an unsaturated bond resulting therefrom, i.e. —CH═CH— moiety is subjected to hydrogenation (addition of hydrogen atoms) using a noble metal catalyst such as palladium to synthesize an aimed polymer. Furthermore, for using in a resist resin, a weight-average molecular weight of the polymer of this invention is preferably selected in the range of 2,000 to 200,000.

The polymer of this invention described above is a polymer suitable for use of a resist resin contained in a chemical-amplification-type resist. In particular, the resist composition of chemical-amplification-type according to this invention can be prepared by blending at least a photo-acid generator capable of generating an acid by exposure as a photo-sensitizer and the polymer of this invention as a resist resin.

Furthermore, since the resist composition of chemical-amplification-type according to this invention is directed to application to photolithography using exposure light at 180 nm or shorter, a photo-acid generator used as a photo-sensitizer therein is desirably such a photo-acid generator that can generate an acid by exposure to light at 130 to 180 nm. For allowing an applied film to be uniformly formed by a film formation method such as spin coating and allowing a thickness of the applied film to be adjusted to at least as fine size as a targeted minimum line width of a fine pattern, the resist composition of chemical-amplification-type according to this invention is prepared in a solution form such that a mixture of components such as the polymer of this invention employed as a resist resin and a photo-acid generator are completely dissolved in an organic solvent. The organic solvent used in the resist composition of chemical-amplification-type according to this invention may be, without limitations, any type of solvent which can completely dissolve the polymer of this invention used as a resist resin and the photo-acid generator employed as a photo-sensitizer and which have fluidity and viscosity suitable for forming of an uniform film applied by a film coating technique such as spin coating. In such a case, the organic solvent can be used alone or in combination of two or more as appropriate.

Examples of an organic solvent meeting the above requirements may include, but, of course, not limited to, such a solvent as n-propyl alcohol, isopropyl alcohol, n-butyl alcohol, tert-butyl alcohol, propyleneglycol monomethyl ether acetate, propyleneglycol monoethyl ether acetate, ethyl lactate, 2-methoxybutyl acetate, 2-ethoxyethyl acetate, methyl pyruvate, ethyl pyruvate, methyl 3-methoxypropionate, ethyl 3-methoxypropionate, N-methyl-2-pyrrolidinone, cyclohexanone, cyclopentanone, cyclohexanol, methyl ethyl ketone, 1,4-dioxane, ethyleneglycol monomethyl ether, ethyleneglycol monoethyl ether acetate, ethyleneglycol monomethyl ether, ethyleneglycol monoisopropyl ether, diethyleneglycol monomethyl ether and diethyleneglycol dimethyl ether.

On the other hand, examples of a photo-acid generator capable of generating an acid by exposure to light at 130 to 180 nm, may include, but not limited to, such a compound as triphenylsulfonium salt derivatives, diphenyliodonium salt derivatives, dialkylphenacylsulfonium salt derivatives, nitrobenzylsulfonate derivatives and N-hydroxysuccinimide sulfonate derivatives. For allowing adequate sensitivity in a film applied of the chemical-amplification-type resist and allowing satisfactory patterning therewith, a content of the photo-acid generator in the resist composition of chemical-amplification-type is preferably 0.2 wt % or more, more preferably 1 wt % or more to the total amount of the polymer of this invention contained as a resist resin and the photo-acid generator. On the other hand, for forming an uniform film coated and preventing a residue (scum) after development, a content of the photo-acid generator is kept at preferably 30 wt % or less, more preferably 15 wt % or less to the total amount of the polymer of this invention and the photo-acid generator. The photo-acid generator can be used alone or in combination of two or more as appropriate.

Furthermore, in addition to the photo-acid generator employed as a photo-sensitizer, the polymer of this invention used as a resist resin and an organic solvent dissolving them, supplemented to the resist composition of chemical-amplification-type according to this invention may be, if necessary, a variety of additives commonly used for the like resists of chemical-amplification-type, for instance, such additional components as dissolution inhibitors, organic bases, surfactants, pigments, stabilizers, application improvers and dyes.

Beside, as the polymer of this invention exhibits high transparency to exposure light at 180 nm or less, it concomitantly exhibits higher transparency to exposure light at longer than 180 nm. Thus, if a photo-acid generator used therein can generate an acid not only by exposure to light at 130 to 180 nm but also effectively generate an acid by irradiation with light at 180 to 220 nm, such a resist composition of chemical-amplification-type according to this invention can be applied to photolithography using light at 180 to 220 nm, for example, ArF excimer laser beam as exposure light.

The resist composition of chemical-amplification-type according to this invention is uniformly applied on a substrate to be processed by an appropriate method such as spin coating to form a film coated in a desired thickness. Then, an intended pattern is exposed thereon with exposure light at 180 nm or less, for instance, at 130 to 180 nm and is subsequently subjected to baking, during of which heat-treatment chemical amplification is carried on by using a proton acid generated from the photo-acid generator as a catalyst therefor. In particular, during the baking treatment, for the repeating units represented by general formulas (1a), (2a), (3a), (3b), (4a) and (4b) contained in the polymer of this invention used as a resist resin, dissociative conversion of a fluorine-containing acetal or ketal structure thereof into —OH is conducted by using the proton acid as a catalyst, and then development is conducted using a basic solution to dissolve and remove the resin in the exposed fine region, which process can be used successfully to form the aimed fine patter. Namely, as illustrated above, a resist composition of chemical-amplification-type according to this invention can be preferably prepared in the form of a positive type resist.

EXAMPLES

This invention will be more specifically explained with reference to examples herein. These examples are just good examples for illustrating the best modes for carrying out this invention, but do not limit the scope of this invention in any manner.

Example 1

As an example of the monomer of (meth)acrylate derivative type represented by general formula (2) described above, methacrylate 1 having the structure below was synthesized, where a choice therefor is made such that $R^1$ is trifluoromethyl group, $R^2$ is difluoromethyl group, $R^3$ is benzyl group, $R^6$ is methyl group and $R^4$ and $R^5$ are hydrogen atoms.

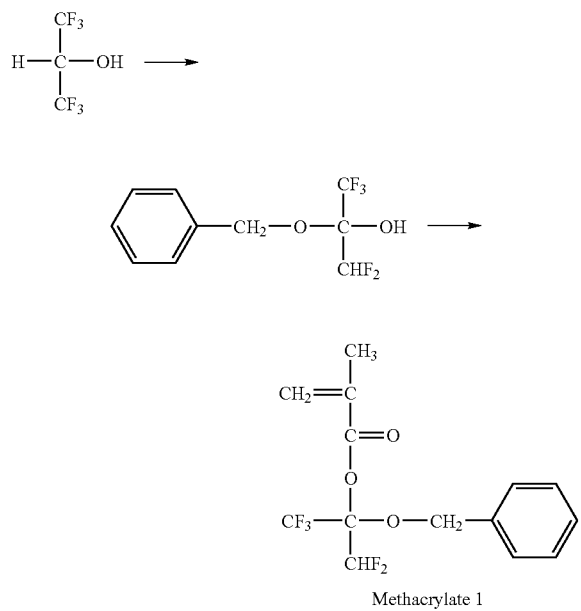

Methacrylate 1

There will be described the process for synthesis of methacrylate 1 and the conditions used therein.

In 70 mL of dry THF was dissolved 8.56 g of hexafluoroisopropanol (($CF_3$)$_2$CH—OH), and the solution was cooled to −78° C. under an argon atmosphere. To the solution was added dropwise 67 mL of a 1.6 mol/L n-butyllithium ($CH_3CH_2CH_2CH_2$—Li) solution in hexane, and then the mixture was stirred at 0° C. for one hour. After that, to the reaction solution was added a solution of 5 g of benzyl alcohol in dry THF, and the mixture was stirred at room temperature for 4.5 hours. The reaction mixture was poured into ice-water. The mixture was made acidic by adding diluted hydrochloric acid and the organic layer was extracted with ether. The extracted ether layer was washed with a saline solution and dried over anhydrous $MgSO_4$. After evaporation of the solvent from the ether layer under a reduced pressure, the residue was distilled under a reduced pressure (64 to 65° C./0.5 mmHg) to provide 3 g of a fluorinated hemiacetal (2-benzyloxy-1,1,1,3,3-pentafluoro-2-propanol) (yield: 16%). Subsequently, in 20 mL of dry dichloromethane were dissolved 2 g of the fluorinated hemiacetal, 2.56 g of triethylamine and 8 mg of phenothiazine. To the solution was added dropwise under ice cooling a solution of 2.21 g of methacryloyl chloride in 4 mL of dichloromethane. After stirring at room temperature for 4 hours, the reaction solution was diluted with 100 mL of ether, sequentially washed with 0.5 N hydrochloric acid, 3% aqueous $NaHCO_3$ solution and a saline solution and dried over anhydrous $MgSO_4$. After evaporating ether under a reduced pressure, the residue was purified by column chromatography on silica gel (eluent: hexane/ethyl acetate=40/1) to obtain 1.7 g of the desired methacrylate 1 (colorless liquid, yield: 67%).

$^1$H-NMR (CDCl$_3$) δ ppm: 1.96 (3H, s), 4.74–4.89 (2H, m), 5.78 (1H, s), 6.27 (1H, s), 6.65 (1H, t), 7.26–7.43 (5H, m);

IR (KBr): 1750 (vC=O), 1638 (vC=C), 1210, 1177, 1141, 1116, 1047 cm$^{-1}$

Example 2

As an example of the monomer of (meth)acrylate derivative type represented by general formula (2) described above, methacrylate 2 represented by the structure below was synthesized, where a choice therefor is made such that $R^1$ is trifluoromethyl group, $R^2$ is difluoromethyl group, $R^3$ is 2-norbornyl methyl group, $R^6$ is methyl group and $R^4$ and $R^5$ are hydrogen atoms.

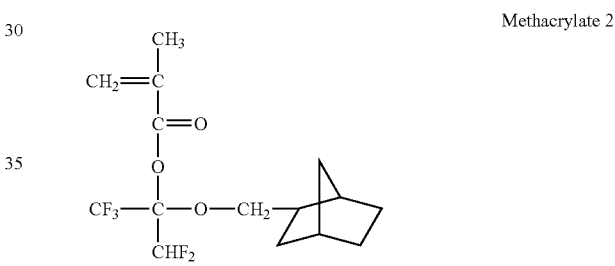

Methacrylate 2

There will be described the process for synthesis of methacrylate 2 and the condition used therein.

A fluorinated hemiacetal (1,1,1,3,3-pentafluoro-2-(2-norbornyl methoxy)-2-propanol), by the way of the intermediate product therefor, was prepared by using 2-norbornanemethanol in place of benzyl alcohol in similar manner to the reaction conditions described in Example 1. Then, as described in Example 1, the fluorinated hemiacetal in the way of the intermediate product and methacryloyl chloride were reacted and the residual material was purified to obtain methacrylate 2 (colorless liquid, yield: 65%) as desired product.

$^1$H-NMR (CDCl$_3$) δ ppm: 0.52–1.82 (9H, m), 1.97 (3H, s), 2.05–2.32 (2H, m), 3.35–3.83 (2H, m), 5.78 (1H, s), 6.27 (1H, s), 6.57 (1H, t);

IR (KBr): 2874, 2958 (vC—H), 1749 (vC=O), 1638 (vC=C), 1210, 1180, 1141, 1118, 1041 cm$^{-1}$

Example 3

As an example of the monomer of (meth)acrylate derivative type represented by general formula (2) described above, acrylate 1 represented by the structure below was synthesized, where a choice therefor is made such that $R^1$ is trifluoromethyl group, $R^2$ is difluoromethyl group, $R^3$ is isobutyl group and $R^4$, $R^5$ and $R^6$ are hydrogen atoms.

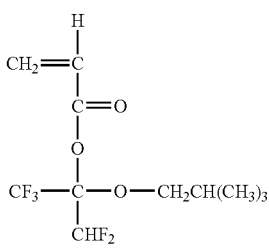

Acrylate 1

There will be described the process for synthesis of acrylate 1 and the conditions used therein.

In 120 mL of dry THF was dissolved 15 g of hexafluoroisopropanol ((CF$_3$)$_2$CH—OH), and the solution was cooled to 0° C. under an argon atmosphere. To the solution was added dropwise 117 mL of a 1.6 mol/L n-butyllithium (CH$_3$CH$_2$CH$_2$CH$_2$—Li) solution in hexane and then the mixture was stirred at 0° C. for one hour and subsequently at room temperature for additional one hour. Next, to the reaction solution was added 6.62 g of isobutyl alcohol, and the mixture was stirred at room temperature overnight. After that, to the solution containing the intermediate product was added dropwise 8.08 g of acryloyl chloride under ice cooling and the mixture was stirred at room temperature for 4 hours. Precipitated lithium chloride was filtered off and the filtrate was concentrated in vacuo. To the residue was added 300 mL of ether. The ethereal layer was washed sequentially with diluted hydrochloric acid, 3% sodium bicarbonate solution and a saline solution and dried over anhydrous MgSO$_4$. The solvent was evaporated from the ethereal layer under a reduced pressure. The residue was purified by column chromatography on silica gel (eluent: hexane/ethyl acetate=20/1) to obtain 4.5 g of the desired acrylate 1 (colorless liquid, yield: 18%).

$^1$H-NMR (CDCl$_3$) δ ppm: 0.91 (6H), 1.82–1.97 (1H, m), 3.43–3.63 (2H, m), 6.05 (1H, d), 6.16 (1H, dd), 6.55 (1H, d), 6.60 (1H, t);

IR (KBr): 2967, 2881 (νC—H), 1761 (νC=O), 1635 (νC=C), 1210, 1186, 1131, 1103, 1042 cm$^{-1}$

Example 4

As an example of the monomer of (meth)acrylate derivative type represented by general formula (2) described above, acrylate 2 represented by the structure below was synthesized, where a choice therefor is made such that R$^1$ is trifluoromethyl group, R$^2$ is difluoromethyl group, R$^3$ is methyl group and R$^4$, R$^5$ and R$^6$ are hydrogen atoms.

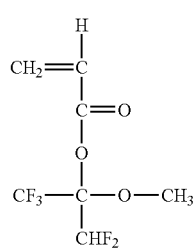

Acrylate 2

There will be described the process for synthesis of acrylate 2 and the conditions used therein.

The process was conducted, in similar manner to the reaction conditions as described in Example 3, by using methanol in place of isobutyl alcohol to obtain the desired acrylate 2 (colorless liquid, yield: 32%).

$^1$H-NMR (CDCl$_3$) δ ppm: 3.57 (3H, s), 6.07 (1H, d), 6.18 (1H, dd), 6.58 (1H, d), 6.56 (1H, t);

IR (KBr): 2965, 2864 (νC—H), 1761 (νC=O), 1635 (νC=C), 1211, 1181, 1133, 1101, 1045 cm$^{-1}$

Example 5

As an example of the monomer of (meth)acrylate derivative type represented by general formula (2) described above, acrylate 3 represented by the structure below was synthesized, where a choice therefor is made such that R$^1$ and R$^2$ are trifluoromethyl groups, R$^3$ is methyl group and R$^4$, R$^5$ and R$^6$ are hydrogen atoms.

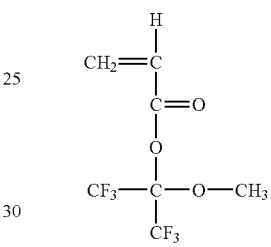

Acrylate 3

There will be described the process for synthesis of acrylate 3 and the conditions used therein.

Into 1.82 g of dry methanol was introduced 18.86 g of hexafluoroacetone, and the mixture was stirred at room temperature. After 6 hours, the reaction mixture was distilled under a reduced pressure, to obtain 11.2 g of hexafluoroacetone methylhemiacetal as an intermediate fluorinated hemiacetal. Next, in 50 mL of THF was dissolved 11.2 g of hexafluoroacetone methylhemiacetal, and the mixture was cooled to −78° C. To the solution was added dropwise 35.5 mL of a n-butyllithium solution in hexane (concentration: 1.6 mol/L). After stirring for one hour, 5.14 g of acryloyl chloride was added dropwise thereto. After stirring for 4 hours under ice cooling, precipitated lithium chloride was filtered off and the filtrate was concentrated in vacuo. To the residue was added 200 mL of ether, and the ethereal layer was sequentially washed with a saline solution and water. The ethereal layer was dried over anhydrous magnesium sulfate. After evaporation of ether under a reduced pressure, the residue was distilled under a reduced pressure to obtain 3.06 g of the desired acrylate 3 (yield: 21%, colorless liquid).

Example 6

As an example of the monomer of norbornene derivative type represented by general formula (3) described above, the norbornene-5-carboxylate represented by the structure below was synthesized, where a choice therefor is made such that m=0, Z is —CO—, R$^1$ is trifluoromethyl group, R$^2$ is difluoromethyl group, R$^3$ is isobutyl group, and R$^4$, R$^5$ and R$^6$ are hydrogen atoms.

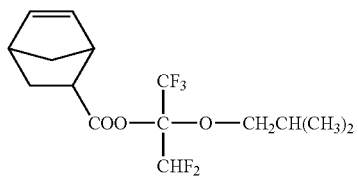

There will be described the process for synthesis of the norbornene derivative and the conditions used therein.

To 3.03 g of acrylate 1 obtained in Example 3 was added dropwise 0.761 g of cyclopentadiene (prepared by pyrolysis of dicyclopentadiene), and the mixture was stirred at room temperature overnight. The unreacted starting materials and impurities were removed under a reduced pressure to obtain 3.64 g of the desired norbornene derivative (colorless liquid, yield: 97%).

$^1$H-NMR (CDCl$_3$) δ ppm: 0.83–0.98 (6H, m), 1.23–1.55 (3H, m), 1.80–2.04 (2H, m), 2.96 (1H, s), 3.04–3.18 (1H, m), 3.28 (1H, s), 3.38–3.62 (2H, m), 5.89–6.29 (2H, m), 6.49–6.55 (1H, t);

IR (KBr): 2879, 2968 (vC—H), 1770 (vC=O), 1042, 1106, 1129, 1183, 1210 cm$^{-1}$

Example 7

As an example of the monomer of norbornene derivative type represented by general formula (3), the 2-norbornene-5-carboxylate represented by the structure below was synthesized, where a choice therefor is made such that m=0, Z is —CO—, R$^1$ is trifluoromethyl group, R$^2$ is difluoromethyl group, R$^3$ is methyl group, and R$^4$, R$^5$ and R$^6$ are hydrogen atoms.

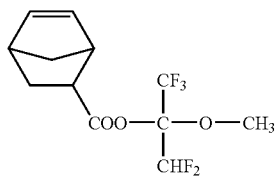

There will be described the process for synthesis of the norbornene derivative and the conditions used therein.

The process was conducted, in similar manner to the reaction conditions as described in Example 6, by using acrylate 2 prepared in Example 4 in place of acrylate 1 prepared in Example 3 to obtain the desired norbornene derivative (boiling point: 69–70° C./0.5 mmHg, colorless liquid, yield: 95%).

$^1$H-NMR (CDCl$_3$) δ ppm: 1.24–1.53 (3H, m), 1.91–2.02 (1H, m), 2.97 (1H, s), 3.09–3.15 (1H, m), 3.30 (1H, s), 3.54–3.57 (3H, s), 5.90–6.31 (2H, m), 6.47–6.53 (1H, t);

IR (KBr): 2877, 2982 (vC—H), 1770 (vC=O), 1043, 1107, 1132, 1178, 1210 cm$^{-1}$

Example 8

As an example of the monomer of tetracyclododecene derivative type represented by general formula (3) described above, the ester derivative of tetracyclododecene-8-carboxylic acid represented by the structure below was synthesized, where a choice therefor is made such that m=1, Z is —CO—, R$^1$ is trifluoromethyl group, R$^2$ is difluoromethyl group, R$^3$ is methyl group, and R$^4$, R$^5$ and R$^6$ are hydrogen atoms.

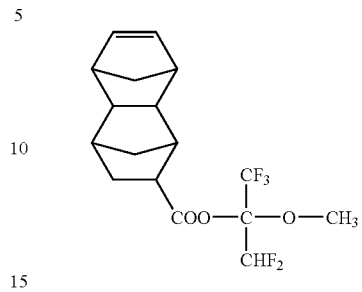

There will be described the process for synthesis of the tetracyclododecene derivative and the conditions used therein.

A mixture of the norbornene derivative obtained in Example 7 and dicyclopentadiene were stirred at 160 to 170° C. for 10 hours. From the reaction mixture, the unreacted dicyclopentadiene was removed by evaporation under a reduced pressure. The residue was purified by silica gel column chromatography (eluent: hexane/ethyl acetate=20/1), to obtain the desired ester derivative of tetracyclo[4.4.0.1$^{2,5}$.1$^{7,10}$]-3-dodecene-8-carboxylic acid (yield: 24%).

Example 9

As an example of the monomer of tricyclononene derivative type represented by general formula (4) described above, the ester derivative of tricyclo-3-nonene-7-carboxylic acid represented by the structure below was synthesized, where a choice therefor is made such that Z is —CO—, R$^1$ is trifluoromethyl group, R$^2$ is difluoromethyl group, R$^3$ is methyl group, and R$^4$, R$^5$ and R$^6$ are hydrogen atoms.

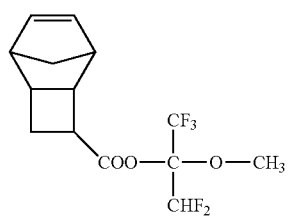

There will be described the process for synthesis of the tricyclononene derivative and the conditions used therein.

A mixture of 8.55 g of acrylate 2 prepared in Example 4 and 3.7 g of quadricyclane was stirred at 90° C. for 24 hours. The unreacted quadricyclane (tetracycle[3.2.0.0$^{2,7}$.0$^{4,6}$]heptane) was removed by evaporation under a reduced pressure. The residue was distilled under a reduced pressure (85–86° C./0.3 mmHg) to obtain 2.9 g of the desired ester derivative of tricyclo[4.2.1.0$^{2,5}$]-3-nonene-6-carboxylic acid (yield: 24%).

Example 10

As an example of the monomer of norbornene derivative type represented by general formula (3) described above, the norbornene derivative represented by the structure below was synthesized, where a choice therefor is made such that m=0, Z is methylene group, $R^1$ and $R^2$ are trifluoromethyl groups, $R^3$ is hydrogen atom, and $R^4$, $R^5$ and $R^6$ are hydrogen atoms.

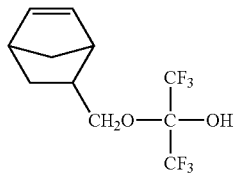

Into 7.05 g of 2-norbornene-5-methanol was introduced 18.86 g of hexafluoroacetone, and the mixture was stirred at room temperature overnight. The reaction mixture was distilled under a reduced pressure to obtain 16.16 g of hexafluoroacetone=(2-norbornen-5-ylmethyl)=hemiacetal (yield: 98%).

$^1$H-NMR (CDCl$_3$) δ ppm: 0.41–0.58 (1H, m), 1.08–1.93 (3H, m), 2.28–2.46 (1H, m), 2.82 (1H, s), 2.94 (1H, s), 3.29–3.99 (3H, m), 5.86–6.24 (2H, m);

IR (KBr): 3435 (vO—H), 2873, 2973 (vC—H), 1770 (vC=O), 1111, 1158, 1224, cm$^{-1}$

Example 11

As an example of the monomer of norbornene derivative type represented by general formula (3) described above, the norbornene derivative represented by the structure below was synthesized, where a choice therefor is made such that m=0, Z is methylene, $R^1$ and $R^2$ are trifluoromethyl groups, $R^3$ is methyl group, and $R^4$, $R^5$ and $R^6$ are hydrogen atoms.

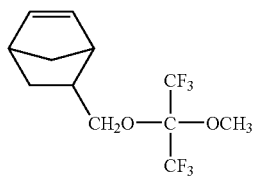

In 10 mL of dry ether was dissolved 1 g of the hemiacetal prepared in Example 10. To the solution were added 0.633 g of potassium carbonate and 0.7 g of methyl p-toluenesulfonate, and the mixture was stirred at room temperature for 12 hours. The reaction mixture was filtered and the filtrate was purified by silica gel column chromatography to obtain 0.47 g of hexafluoroacetone=methyl=(2-norbornen-5-ylmethyl)acetal (yield: 45%).

Example 12

As an example of the polymer comprising the repeating unit represented by general formula (2a) described above, there was synthesized a polymer comprising a repeating unit represented by general formula (2a) in a content of 100 mol %, in which a choice therefor is made such that $R^1$ is trifluoromethyl group, $R^2$ is difluoromethyl group, $R^3$ is norbornylmethyl group, $R^4$ and $R^5$ are hydrogen atoms, and $R^6$ is methyl group.

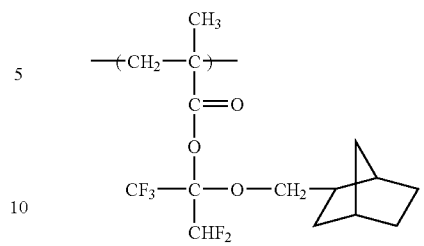

There will be described the process for synthesis of the polymer of polymethacrylate type and the conditions used therein.

In a 50 mL egg-plant shaped flask equipped with a reflux condenser, 6.4 g of methacrylate 2 prepared in Example 2 was dissolved in 16 mL of dry toluene. To the solution was added 123 mg of azobisisobutyronitrile (AIBN) (4 mol %) as an initiator for polymerization, and the mixture was stirred at 80° C. under an argon atmosphere. After stirring 12 hours, the reaction mixture was allowed to be cooled and poured into 200 mL of hexane. The precipitate was collected by filtration and further purified by reprecipitation to obtain 0.65 g of the desired polymer (yield: 10%). As determined by GPC analysis, the polymer obtained showed a weight-average molecular weight (Mw) of 7800 (calculated in polystyrene equivalent) and a ratio of weight-average molecular weight (Mw) to number-average molecular weight (Mn), i. e., a dispersion index (Mw/Mn) of 1.98.

Example 13

As an example of the polymer comprising the repeating unit represented by general formula (2a) described above, there was synthesized a copolymer comprising the repeating unit of general formula (2a) in a content of 80 mol %, in which a choice therefor is made such that $R^1$ is trifluoromethyl group, $R^2$ is difluoromethyl group, $R^3$ is norbornylmethyl group, $R^4$ and $R^5$ are hydrogen atoms, and $R^6$ is methyl group, and the repeating unit of general formula (5) in a content of 20 mol %, in which a choice therefor is made such that $R^7$ and $R^8$ are hydrogen atoms, $R^9$ is methyl group and $R^{10}$ is tert-butyl group.

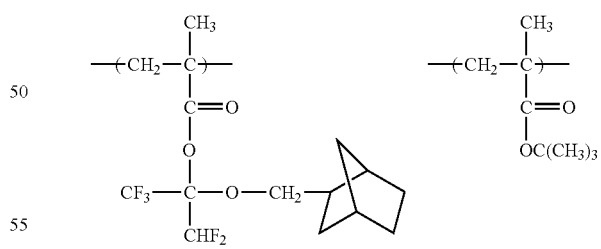

There will be described the process for synthesis of the copolymer of polymethacrylate type and the conditions used therein.

In an egg-plant shaped flask equipped with a reflux condenser, 2.5 g of methacrylate 2 prepared in Example 2 and 0.538 g of tert-butyl methacrylate were dissolved in 10 mL of tetrahydrofuran. To the solution was added 0.099 g of AIBN as an initiator for polymerization, and the mixture was stirred under an argon atmosphere at 65° C. for 12 hours. After being allowed to be cooled, the reaction mixture was poured into 100 mL of hexane. The precipitated polymer was collected by filtration and purified by reprecipitation to obtain 2 g of the desired copolymer (yield: 36%). As determined by GPC analysis, the copolymer obtained showed an weight-average molecular weight (Mw) of 10800 (calculated in polystyrene equivalent) and a dispersion index (Mw/Mn) of 1.84.

Example 14

As an example of the polymer comprising the repeating unit represented by general formula (2a) described above, there was synthesized a copolymer comprising a repeating unit of general formula (2a) in a content of 70 mol %, in which a choice therefor is made such that $R^1$ is trifluoromethyl group, $R^2$ is difluoromethyl group, $R^3$ is norbornylmethyl group, $R^4$ and $R^5$ are hydrogen atoms, and $R^6$ is methyl group, and a styrene type repeating unit of general formula (6) in a content of 30 mol %, in which a choice therefor is made such that $R^{11}$ is tert-butoxycarbonyl group.

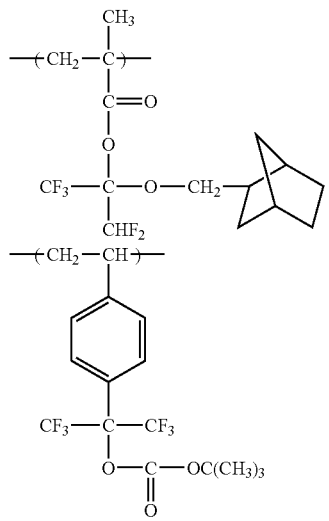

There will be described the process for synthesis of said copolymer and the conditions used therein.

5 g of methacrylate 2 prepared in Example 2 was reacted with 2.4 g of 4-(hexafluoro-2-(tert-butoxycarbonyloxy)isopropyl)styrene, in place of tert-butyl methacrylate, in similar manner to the polymerization conditions described in Example 13 to prepare the copolymer composed of the two repeating units described above (yield: 40%). As determined by GPC analysis, the copolymer obtained showed a weight-average molecular weight (Mw) of 9500 (calculated in polystyrene equivalent) and a dispersion index (Mw/Mn) of 2.11.

Example 15

As an example of the polymer comprising the repeating unit represented by general formula (2a) described above, there was synthesized a copolymer comprising a repeating unit of general formula (2a) in a content of 70 mol %, in which a choice therefor is made such that $R^1$ is trifluoromethyl group, $R^2$ is difluoromethyl group, $R^3$ is norbornylmethyl group, $R^4$ and $R^5$ are hydrogen atoms, and $R^6$ is methyl group, and a styrene type repeating unit of general formula (6) in a content of 30 mol %, in which a choice therefor is made such that $R^{11}$ is hydrogen atom.

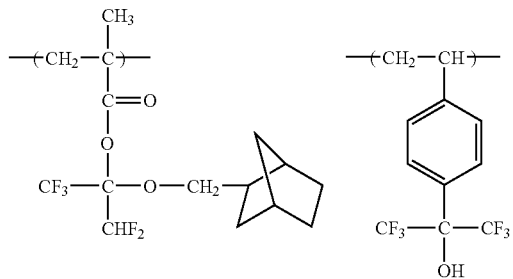

There will be described the process for synthesis of said copolymer and the conditions used therein.

5 g of methacrylate 2 prepared in Example 2 was reacted with 1.75 g of 4-(hexafluoro-2-hydroxyisopropyl)styrene, in place of tert-butyl methacrylate, in similar manner to the polymerization conditions described in Example 13 to prepare the copolymer composed of the two repeating units described above (yield: 40%). As determined by GPC analysis, the copolymer obtained showed a weight-average molecular weight (Mw) of 9500 (calculated in polystyrene equivalent) and a dispersion index (Mw/Mn) of 2.11.

Example 16

As an example of the polymer comprising the repeating unit represented by general formula (3a) described above, there was synthesized a polymer comprising the repeating unit of general formula (3a) in a content of 100 mol %, in which a choice therefor is made such that m=0, Z is —CO—, $R^1$ is trifluoromethyl group, $R^2$ is difluoromethyl group, $R^3$ is methyl group, and $R^4$, $R^5$ and $R^6$ are hydrogen atoms.

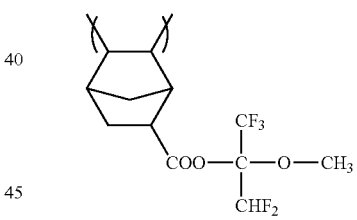

There will be described the process for synthesis of the polymer of polynorbornene type and the conditions used therein.

In 3 mL of dichloromethane were dissolved 0.0182 g of di-μ-chlorobis[(η-allyl)palladium(II)] and 0.0453 g of silver hexafluoroantimonate (AgSbF$_6$), and the mixture was stirred at room temperature. After 20 min, the reaction mixture was filtered. To the filtrate was added a solution of 1.489 g of the norbornene derivative (2-methoxy-1,1,1,3,3-pentafluoroisopropyl 2-norbornene-5-carboxylate) prepared in Example 7 and 0.011 g of N,N,N',N'-tetramethyl-1,8-naphthalenediamine in 2 mL of dichloromethane. The addition was followed by stirring at room temperature for further 20 hours. After that, the mixture was poured into 50 mL of methanol. The precipitated resin was collected by filtration to obtain 0.715 g of the desired polymer (yield: 48%). As determined by GPC analysis, the polymer obtained showed a weight-average molecular weight (Mw) of 18500 (calculated in polystyrene equivalent) and a dispersion index (Mw/Mn) of 2.44.

Example 17

As an example of the polymer comprising the repeating unit represented by general formula (3a) described above, there was synthesized a copolymer comprising the repeating unit of general formula (3a) in a content of 70 mol %, in which a choice therefor is made such that m=0, Z is —CO—, $R^1$ is trifluoromethyl group, $R^2$ is difluoromethyl group, $R^3$ is methyl group, and $R^4$, $R^5$ and $R^6$ are hydrogen atoms, and the norbornene type repeating unit of general formula (7) in a content of 30 mol %, in which a choice therefor is made such that $R^{12}$ is tert-butoxycarbonyl group.

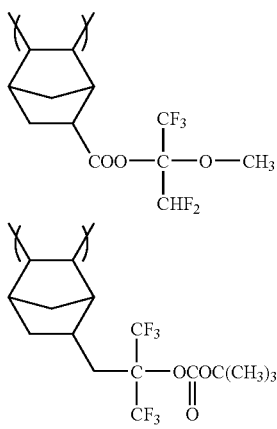

There will be described the process for synthesis of the polymer of polynorbornene type and the conditions used therein.

In 6 mL of dichloromethane were dissolved 0.0364 g of di-μ-chlorobis[(η-allyl)palladium(II)] and 0.0906 g of silver hexafluoroantimonate ($AgSbF_6$), and the mixture was stirred at room temperature. After 20 min, the reaction mixture was filtered. To the filtrate was added a solution of 2.08 g of the norbornene derivative (2-methoxy-1,1,1,3,3-pentafluoroisopropyl 2-norbornene-5-carboxylate) prepared in Example 7, 1.114 g of 5-(1,1,1,3,3,3-hexafluoro-2-(tert-butoxycarbonyloxy)propan-2-yl)-2-norbornene and 0.022 g of N,N,N',N'-tetramethyl-1,8-naphthalenediamine in 4 mL of dichloromethane. The addition was followed by stirring at room temperature for further 20 hours. After that, the mixture was poured into 100 mL of methanol. The precipitated resin was collected by filtration to obtain 1.34 g of the desired copolymer (yield: 42%). As determined by GPC analysis, the copolymer obtained showed a weight-average molecular weight (Mw) of 19600 (calculated in polystyrene equivalent) and a dispersion (Mw/Mn) of 2.36.

Example 18

As an example of the polymer comprising the repeating unit represented by general formula (4a) described above, there was synthesized a copolymer comprising the repeating unit of general formula (4a) in a content of 70 mol %, in which a choice therefor is made such that Z is —CO—, $R^1$ is trifluoromethyl group, $R^2$ is difluoromethyl group, $R^3$ is methyl group, and $R^4$, $R^5$ and $R^6$ are hydrogen atoms, and the norbornene type repeating unit of general formula (7) in a content of 30 mol %, in which a choice therefor is made such that $R^{12}$ is tert-butoxycarbonyl group.

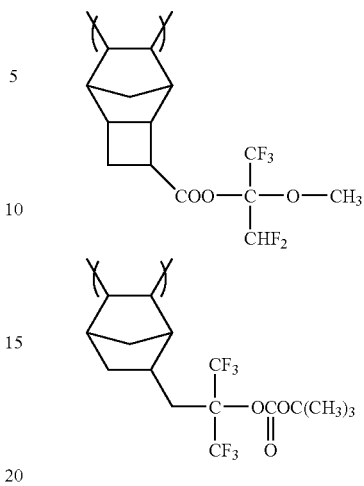

There will be described the process for synthesis of the polymer of polynorbornene type and the conditions used therein.

2.27 g of tricyclononene derivative prepared in Example 9, in place of the norbornene derivative prepared in Example 7, was reacted with 1.114 g of 5-(1,1,1,3,3,3-hexafluoro-2-(tert-butoxycarbonyloxy)propan-2-yl)-2-norbornene in similar manner to the polymerization conditions described in Example 17 to prepare the desired copolymer (yield: 40%). As determined by GPC analysis, the copolymer obtained showed a weight-average molecular weight (Mw) of 21500 (calculated in polystyrene equivalent) and a dispersion index (Mw/Mn) of 2.42.

Example 19

Evaluation of Transparency of Polymers

In 0.45 g of propyleneglycol monomethyl ether acetate was dissolved 0.08 g of the resin prepare in Example 12, and the mixture was filtered through a Teflon® filter with cut-off size of 0.2 μm. Then, the solution thus obtained was applied on a calcium fluoride disk by spin coating and the disk was baked on a hot plate at 110° C. for 120 sec to form a thin film with a thickness of 0.3 μm. The thin film was measured for a transmittance at the lasing wavelength of $F_2$ excimer laser beam of 157 nm using a vacuum ultraviolet spectrophotometer (Nihon Bunko, VUV-201).

Under the same process and conditions, the resins prepared in Examples 13, 14, 16 and 17 were also used to form thin films with a thickness of 0.3 μm, which was then measured for a transmittance at 157 nm. As a comparative example, under the same process and conditions, a resist resin used as a resin for KrF excimer laser beam exposure; i.e. poly(p-hydroxy styrene) was also used to form a thin film with a thickness of 0.3 μm, which was measured for a transmittance at 157 nm. The observed curve for a transmittance per 0.1 μm of the applied film as for the resin obtained in Example 12 is shown in FIG. 1.

The measurement results show that the observed transmittance value for each applied film at 157 nm was 47%/0.1 μm for the polymer resins obtained in Example 12, 43%/0.1 μm for the polymer resins obtained in Example 13, 48%/0.1 μm for the polymer resins obtained in Example 14, 50%/0.1 μm for the polymer resins obtained in Example 16, and 56%/0.1 μm ofr the polymer resings obtained in Example 17, and 20%/0.1 μm for poly(p-hydroxy styrene), respectively. From these results, it can be confirmed that the polymer resin according to this invention exhibits high transparency to light at a wavelength of 157 nm.

Example 20

Exposure Performance of a Chemical Amplification Resist Composition Employing the Polymer According to this Invention as a Resist Resin Therefor A chemical amplification resist composition having the following composition was prepared, which used the copolymer prepared in Example 13 as a resist resin therefor.

Resist Composition:
(a) the polymer (Example 13): 1.5 g
(b) a photo-acid generator (triphenylsulfonium nonaflate): 0.015 g
(c) propyleneglycol monomethyl ether acetate: 10 g A uniformly blended mixture having the above composition was filtered through a Teflon® filter with cut-off size of 0.2 μm to prepare the resist composition. The resist composition was evaluated for its exposure performance in the following procedure.

On a 4 inch silicon substrate was applied the resist composition by spin coating, and the substrate was pre-baked on a hot plate at 110° C. for 2 min to form a thin-coated resist film with a thickness of 0.1 μm. The thin-coated resist film was exposed to $F_2$ excimer laser as exposure light over an exposure area of 5 mm square. Immediately after exposure, the substrate was post-baked on a-hot plate at 130° C. for 60 sec and then the resin film exposed was developed by 60 sec immersion in a 2.38% aqueous solution of TMAH $((CH_3)_4NOH)$ at 23° C. After the immersion, the thin-coated resist film being developed was rinsed with pure water for 60 sec.

Relationship between a light quantity for exposure and a remaining film thickness in the exposure area was investigated. The results show that for the chemical amplification resist composition described above, the remaining resist film thickness reaches 0 when an exposure light quantity from the $F_2$ excimer laser increases up to 12 $mJ/cm^2$, and the resist composition exhibited behaviors fit to a positive-type resist.

In addition to the chemical amplification resist composition utilizing the copolymer prepared in Example 13 as a resist resin therefor, two types of chemical amplification resist compositions were prepared, which have a corresponding resist composition employing the copolymers obtained in Examples 14 and 17 as a resist resin therefor, respectively. These two types of chemical amplification resist compositions were also evaluated for their exposure performances under the same procedure and conditions. The results show that for the chemical amplification resist composition using the copolymer obtained in Example 14 as a resist resin, a remaining resist film thickness reaches 0 when an exposure light quantity from the $F_2$ excimer laser increases up to 18 $mJ/cm^2$, and for the chemical amplification resist composition comprising using the copolymer obtained in Example 17, a remaining resist film thickness reaches 0 when an exposure light quantity from the $F_2$ excimer laser increases up to 17 $mJ/cm^2$. It was revealed that both the resist compositions exhibited behaviors fit to a positive-type resist.

Example 21

The norbornene derivative obtained in Example 7 is subjected to ring-opening metathesis polymerization using a metathesis catalyst. Then, a —CH=CH— moiety contained in the principal chain of the resulting ring-opened polymer is hydrogenated by using a noble metal catalyst such as palladium to prepare a desired polymer having a saturated principal chain. This polymer is also evaluated for a transmittance of a coated resin film at 157 nm under the procedure and the conditions described in Example 19. Said polymer exhibits excellent transparency to light at a wavelength of 157 nm.

INDUSTRIAL APPLICABILITY

A monomer according to this invention makes use of a fluorine-containing acetal or ketal structure as a moiety to be subjected to an acid-catalytic dissociation with a proton acid derived from a photo-acid generator as well as a principal frame that contains a carbon-carbon double bond exhibiting polymerization activities adaptable to addition polymerization or ring-opening metathesis polymerization. Accordingly, in a polymer of this invention that comprises a repeating unit being obtainable by polymerizing said monomer, optical absorption to exposure light at 180 nm or shorter is significantly reduced. Such a resist of chemical-amplification type that employs the polymer of this invention can make the best use of the aforementioned properties thereof, so that the resist is superior in transparency to exposure light at 180 nm or shorter. For instance, when the resist is applied to photolithography using $F_2$ excimer laser at a lasing wavelength of 157 nm for exposure, it allows to avoid the main cause for inhibition of effective transmission of exposure light to a substrate surface, i.e., such a phenomenon that major part of the exposure light is absorbed by the resin itself placing near top surface of the resist. Accordingly, fine patterning required for process of manufacturing a semiconductor device can be successfully conducted by applying the chemical-amplification-type resist of this invention to photolithography using exposure light at 180 nm or shorter, for example, $F_2$ excimer laser at an emission wavelength of 157 nm.

The invention claimed is:

1. A monomer containing a carbon-carbon double bond exhibiting polymerization activity thereby and having a fluorine-containing structure in the molecule,
wherein the monomer is a (meth)acrylate derivative having a fluorine-containing structure represented by general formula (2):

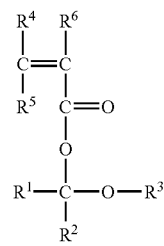

wherein
$R^1$ and $R^2$ independently represent a radical selected from the group consisting of a fluorinated alkyl group and a fluorinated aryl group having 1 to 20 carbon atoms; and at least one of $R^1$ and $R^2$ is said fluorinated alkyl group;
$R^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

$R^4$ and $R^5$ independently represent a hydrogen atom or a fluorine atom; and $R^6$ represents a hydrogen atom, a fluorine atom, a methyl group or a trifluoromethyl group.

2. A polymer being producible by polymerization of one or more monomer materials containing a carbon-carbon double bond exhibiting polymerization activity thereby, wherein the polymer comprises a repeating unit being obtainable by addition polymerization of at least one of the monomer as claimed in claim 1, as one of the repeating units contained in the polymer.

3. A resist composition of chemical-amplification-type comprising a resist resin and a photo-sensitizer therefor, wherein the composition comprises the polymer as claimed in claim 2 as said resist resin.

4. A monomer containing a carbon-carbon double bond exhibiting polymerization activity thereby and having a fluorine-containing structure in the molecule, wherein the monomer is a norbornene derivative or tetracyclododecene derivative having a fluorine-containing structure represented by general formula (3):

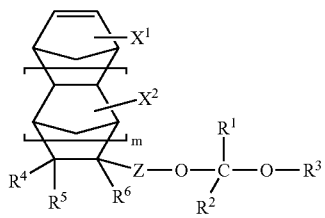

(3)

wherein $R^1$ and $R^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of $R^1$ and $R^2$ is said fluorinated alkyl group or said fluorinated aryl group;

$R^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

$R^4$ and $R^5$ independently represent a hydrogen atom or a fluorine atom;

$R^6$ represents a hydrogen atom, a fluorine atom, a methyl group or a trifluoromethyl group;

$X^1$ and $X^2$ independently represent a hydrogen atom or a methyl group;

Z represents —CO—; and m is 0 or 1.

5. A polymer being producible by polymerization of one or more monomer materials containing a carbon-carbon double bond exhibiting polymerization activity thereby, wherein the polymer comprises a repeating unit being obtainable by ring-opening metathesis polymerization of at least one of the monomer as claimed in claim 4 and then hydrogenating a —CH=CH— moiety resulting therefrom, as one of the repeating units contained in the polymer.

6. A resist composition of chemical-amplification-type comprising a resist resin and a photo-sensitizer therefor, wherein the composition comprises the polymer as claimed in claim 5 as said resist resin.

7. A monomer containing a carbon-carbon double bond exhibiting polymerization activity thereby and having a fluorine-containing structure in the molecule, wherein the monomer is a tricyclononene derivative having a fluorine-containing structure represented by general formula (4):

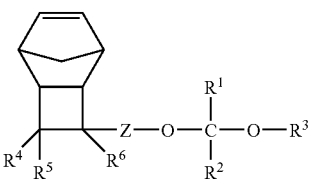

(4)

wherein $R^1$ and $R^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of $R^1$ and $R^2$ is said fluorinated alkyl group or said fluorinated aryl group;

$R^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

$R^4$ and $R^5$ independently represent a hydrogen atom or a fluorine atom;

$R^6$ represents a hydrogen atom, a fluorine atom, a methyl group or a trifluoromethyl group; and Z represents —CO—, a methylene group or a linking group composed of a carbon-oxygen bond.

8. A polymer being producible by polymerization of one or more monomer materials containing a carbon-carbon double bond exhibiting polymerization activity thereby, wherein the polymer comprises a repeating unit being obtainable by ring-opening metathesis polymerization of at least one of the monomer as claimed in claim 7 and then hydrogenating a —CH=CH— moiety resulting therefrom, as one of the repeating units contained in the polymer.

9. A resist composition of chemical-amplification-type comprising a resist resin and a photo-sensitizer therefor, wherein the composition comprises the polymer as claimed in claim 8 as said resist resin.

10. A polymer comprising one or more repeating units being obtainable by addition polymerization of a (meth)acrylate derivative, wherein the unit has a fluorine-containing structure represented by general formula (2a):

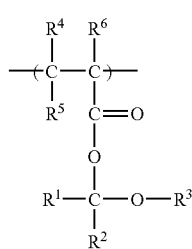

(2a)

wherein $R^1$ and $R^2$ independently represent a radical selected from the group consisting of a fluorinated alkyl group and a fluorinated aryl group having 1 to 20 carbon atoms; and at least one of $R^1$ and $R^2$ is said fluorinated alkyl;

$R^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

$R^4$ and $R^5$ independently represent a hydrogen atom or a fluorine atom; and $R^6$ represents a hydrogen atom, a fluorine atom, a methyl group or a trifluoromethyl group.

11. The polymer as claimed in claim 10, comprising, in addition to said repeating unit having a fluorine-containing structure, one or more repeating units selected from the group consisting of a repeating unit represented by general formula (5):

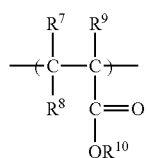

(5)

wherein $R^7$ and $R^8$ are independently a hydrogen atom or a fluorine atom;

$R^9$ is a hydrogen atom, a fluorine atom, a methyl group or a trifluoromethyl group;

$R^{10}$ represents a radical selected from the group consisting of a hydrogen atom; a linear, branched or cyclic alkyl group and fluorinated alkyl group having 1 to 20 carbon atoms; a group removable by an acid; a bridged cyclic hydrocarbon group having 7 to 13 carbon atoms containing a group removable by an acid thereon and norbornane-2,6-carbolactone-5-yl group;

a repeating unit represented by general formula (6):

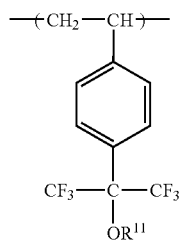

(6)

wherein $R^{11}$ represents a hydrogen atom or a group removable by an acid;

a repeating unit represented by general formula (7):

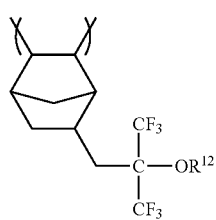

(7)

wherein $R^{12}$ represents a hydrogen atom or a group removable by an acid;

a tetrafluoroethylene radical represented by formula (8):

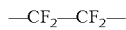

—$CF_2$—$CF_2$— (8)

a repeating unit represented by general formula (9):

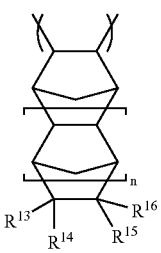

(9)

wherein $R^{13}$ and $R^{14}$ independently represent a hydrogen atom or a fluorine atom; $R^{15}$ represents a hydrogen atom, a fluorine atom, a methyl group or a trifluoromethyl group; $R^{16}$ represents a hydrogen atom, a hydroxy group, hydroxy alkyl group or an acid-dissociable organic group having 20 or less carbon atoms which can generate a carboxy group therefrom by its decomposition by an acid;

a repeating unit represented by general formula (10):

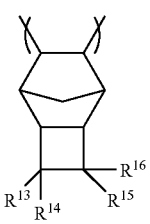

(10)

wherein $R^{13}$ and $R^{14}$ independently represent a hydrogen atom or a fluorine atom; $R^{15}$ represents a hydrogen atom, a fluorine atom, a methyl group or a trifluoromethyl group; $R^{16}$ represents a hydrogen atom, a hydroxy group, a hydroxy alkyl group or an acid-dissociable organic group having 20 or less carbon atoms which can generate a carboxy group therefrom by its decomposition by an acid;

a repeating unit represented by general formula (11):

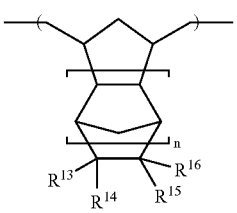

(11)

wherein $R^{13}$ and $R^{14}$ is independently a hydrogen atom or a fluorine atom; $R^{15}$ represents a hydrogen atom, a fluorine atom, a methyl group or a trifluoromethyl group; $R^{16}$ represents a hydrogen atom, a hydroxy group, a hydroxy alkyl group or an acid-dissociable organic group having 20 or less carbon atoms which can generate a carboxy group therefrom by its decomposition by an acid;
a repeating unit represented by general formula (12):

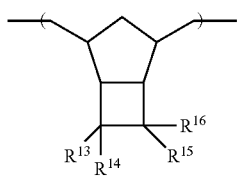

(12)

wherein $R^{13}$ and $R^{14}$ is independently a hydrogen atom or a fluorine atom; $R^{15}$ represents a hydrogen atom, a fluorine atom, a methyl group or a trifluoromethyl group; $R^{16}$ represents a hydrogen atom, a hydroxy group, a hydroxy alkyl group or an acid-dissociable organic group having 20 or less carbon atoms which can generate a carboxy group therefrom by its decomposition by an acid; and
an anhydrous succindiyl represented by formula (13):

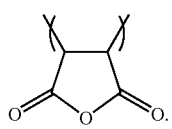

(13)

12. The polymer as claimed in claim 10, wherein the polymer comprises said repeating unit represented by general formula (2a) in a content of at least 5 to 90 mol % to the total number of the repeating units composing the polymer.

13. The polymer as claimed in claim 10, wherein a weight-average molecular weight of the polymer is selected in the range of 2,000 to 200,000.

14. A resist composition of chemical-amplification-type comprising a resist resin and a photo-sensitizer,
wherein the composition comprises one or more of the polymers as claimed in claim 10 as said resist resin and at least a photo-acid generator capable of generating an acid by exposure light as said photo-sensitizer; and
the content of the photo-acid generator to the total amount of the polymer and the photo-acid generator is selected in the range of 0.2 to 30 wt %.

15. A process for formation of pattern by photolithography utilizing a chemical-amplification-type resist, comprising at least the steps of:
forming a film of the chemical-amplification-type resist as claimed in claim 14 applied onto a substrate to be processed for formation of pattern thereon;
irradiating the substrate with light at a wavelength of 130 to 180 nm as exposure light in accordance with a pattern to be formed to expose said film of the chemical-amplification-type resist;
carrying out baking treatment for said exposed film of the chemical-amplification-type resist; and
carrying out developing treatment for said film treated by baking.

16. The process for formation of pattern as claimed in claim 15, wherein the light at a wavelength of 130 to 180 nm used in said exposure step is $F_2$ excimer laser beam.

17. A polymer comprising one or more repeating units being obtainable by addition polymerization of a norbornene derivative or a tetracyclododecene derivative, wherein the unit has a fluorine-containing structure represented by general formula (3a):

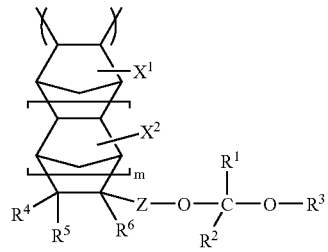

(3a)

wherein
$R^1$ and $R^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of $R^1$ and $R^2$ is said fluorinated alkyl group or said fluorinated aryl group;
$R^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;
$R^4$ and $R^5$ independently represent a hydrogen atom or a fluorine atom;
$R^6$ represents a hydrogen atom, a fluorine atom, a methyl group or a trifluoromethyl group;
$X^1$ and $X^2$ independently represent a hydrogen atom or a methyl group;
Z represents —CO—; and
m is 0 or 1.

18. The polymer as claimed in claim 17, wherein the polymer comprises said repeating unit represented by general formula (3a) in a content of at least 5 to 90 mol % to the total number of the repeating units composing the polymer.

19. A resist composition of chemical-amplification-type comprising a resist resin and a photo-sensitizer,
wherein the composition comprises one or more of the polymers as claimed in claim 17 as said resist resin and at least a photo-acid generator capable of generating an acid by exposure light as said photo-sensitizer; and
the content of the photo-acid generator to the total amount of the polymer and the photo-acid generator is selected in the range of 0.2 to 30 wt %.

20. A polymer comprising one or more repeating units being obtainable by addition polymerization of a tricyclononene derivative, wherein the unit has a fluorine-containing structure represented by general formula (4a):

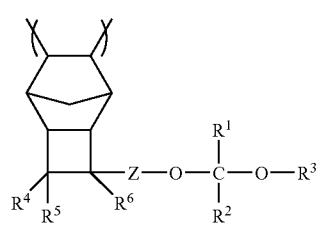

(4a)

wherein

R$^1$ and R$^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of R$^1$ and R$^2$ is said fluorinated alkyl group or said fluorinated aryl group;

R$^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

R$^4$ and R$^5$ independently represent a hydrogen atom or a fluorine atom;

R$^6$ represents a hydrogen atom, a fluorine atom, a methyl group or a trifluoromethyl group; and Z represents —CO—, a methylene group or a linking group composed of a carbon-oxygen bond.

21. The polymer as claimed in claim 20, wherein the polymer comprises said repeating unit represented by general formula (4a) in a content of at least 5 to 90 mol % to the total number of the repeating units composing the polymer.

22. A resist composition of chemical-amplification-type comprising a resist resin and a photo-sensitizer, wherein the composition comprises one or more of the polymers as claimed in claim 20 as said resist resin and at least a photo-acid generator capable of generating an acid by exposure light as said photo-sensitizer; and the content of the photo-acid generator to the total amount of the polymer and the photo-acid generator is selected in the range of 0.2 to 30 wt %.

23. A process for formation of pattern by photolithography utilizing a chemical-amplification-type resist, comprising at least the steps of:

forming a film of the chemical-amplification-type resist as claimed in claim 22 applied onto a substrate to be processed for formation of pattern thereon;

irradiating the substrate with light at a wavelength of 130 to 180 nm as exposure light in accordance with a pattern to be formed to expose said film of the chemical-amplification-type resist;

carrying out baking treatment for said exposed film of the chemical-amplification-type resist; and carrying out developing treatment for said film treated by baking.

24. A polymer comprising one or more repeating units being obtainable by ring-opening polymerization of a norbornene derivative or tetracyclododecene derivative and then hydrogenating a —CH═CH— moiety resulting therefrom, wherein the unit has a fluorine-containing structure represented by general formula (3b):

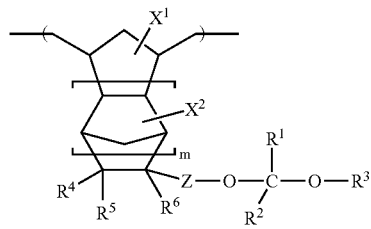

(3b)

wherein

R$^1$ and P$^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of R$^1$ and R$^2$ is said fluorinated alkyl group or said fluorinated aryl group;

R$^3$ represents a radical selected from the group consisting of a hydrogen atom, a linear, branched or cyclic alkyl group, an alkoxy-substituted alkyl group, a fluorinated alkyl group, an aryl group, a fluorinated aryl group, an aralkyl group and a fluorinated aralkyl group having 1 to 20 carbon atoms;

R$^4$ and R$^5$ independently represent a hydrogen atom or a fluorine atom;

R$^6$ represents a hydrogen atom, a fluorine atom, a methyl group or a trifluoromethyl group;

X$^1$ and X$^2$ independently represent a hydrogen atom or a methyl group;

Z represents —CO—, a methylene group or a linking group composed of a carbon-oxygen bond; and m is 0 or 1.

25. The polymer as claimed in claim 24, wherein the polymer comprises said repeating unit represented by general formula (3b) in a content of at least 5 to 90 mol % to the total number of the repeating units composing the polymer.

26. A resist composition of chemical-amplification-type comprising a resist resin and a photo-sensitizer, wherein the composition comprises one or more of the polymers as claimed in claim 24 as said resist resin and at least a photo-acid generator capable of generating an acid by exposure light as said photo-sensitizer; and the content of the photo-acid generator to the total amount of the polymer and the photo-acid generator is selected in the range of 0.2 to 30 wt %.

27. A process for formation of pattern by photolithography utilizing a chemical-amplification-type resist, comprising at least the steps of:

forming a film of the chemical-amplification-type resist as claimed in claim 26 applied onto a substrate to be processed for formation of pattern thereon;

irradiating the substrate with light at a wavelength of 130 to 180 nm as exposure light in accordance with a pattern to be formed to expose said film of the chemical-amplification-type resist;

carrying out baking treatment for said exposed film of the chemical-amplification-type resist; and carrying out developing treatment for said film treated by baking.

28. A polymer comprising one or more repeating units being obtainable by ring-opening polymerization of a tricyclononene derivative and then hydrogenating a —CH═CH— moiety resulting therefrom, wherein the unit has a fluorine-containing structure represented by general formula (4b):

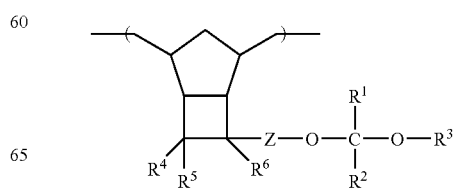

(4b)

wherein $R^1$ and $R^2$ independently represent a radical selected from the group consisting of a hydrogen atom, a linear, branched or cyclic alkyl group, a fluorinated alkyl group, an aryl group and a fluorinated aryl group having 1 to 20 carbon atoms; and at least one of $R^1$ and $R^2$ is said fluorinated alkyl group or said fluorinated aryl group;

$R^3$ represents a radical selected from the group consisting of a hydrogen atom, a linear, branched or cyclic alkyl group, an alkoxy-substituted alkyl group, a fluorinated alkyl group, an aryl group, a fluorinated aiyl group, an aralkyl group and a fluorinated aralkyl group having 1 to 20 carbon atoms;

$R^4$ and $R^5$ independently represent a hydrogen atom or a fluorine atom;

$R^6$ represents a hydrogen atom, a fluorine atom, a methyl group or a trifluoromethyl group; and Z represents —CO—, a methylene group or a linking group composed of a carbon-oxygen bond.

29. The polymer as claimed in claim 28, wherein the polymer comprises said repeating unit represented by general formula (4b) in a content of at least 5 to 90 mol % to the total number of the repeating units composing the polymer.

30. A resist composition of chemical-amplification-type comprising a resist resin and a photo-sensitizer, wherein the composition comprises one or more of the polymers as claimed in claim 28 as said resist resin and at least a photo-acid generator capable of generating an acid by exposure light as said photo-sensitizer; and the content of the photo-acid generator to the total amount of the polymer and the photo-acid generator is selected in the range of 0.2 to 30 wt %.

31. A process for formation of pattern by photolithography utilizing a chemical-amplification-type resist, comprising at least the steps of:

forming a film of the chemical-amplification-type resist as claimed in claim 30 applied onto a substrate to be processed for formation of pattern thereon;

irradiating the substrate with light at a wavelength of 130 to 180 nm as exposure light in accordance with a pattern to be formed to expose said film of the chemical-amplification-type resist;

carrying out baking treatment for said exposed film of the chemical-amplification-type resist; and carrying out developing treatment for said film treated by baking.

* * * * *